(12) United States Patent
Tovey et al.

(10) Patent No.: US 9,188,580 B2
(45) Date of Patent: *Nov. 17, 2015

(54) GENE REPORTER ASSAY, KIT, AND CELLS FOR DETERMINING THE PRESENCE AND/OR THE LEVEL OF A MOLECULE THAT ACTIVATES SIGNAL TRANSDUCTION ACTIVITY OF A CELL SURFACE PROTEIN

(75) Inventors: Michael G. Tovey, Paris (FR); Christophe Lallemand, Paris (FR)

(73) Assignees: LE CENTRE NATIONALE DE LA RECHERCHE SCIENTIFIQUE, Paris (FR); BIOMONITOR LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/336,121

(22) Filed: Dec. 16, 2008

(65) Prior Publication Data

US 2009/0162889 A1 Jun. 25, 2009

Related U.S. Application Data

(63) Continuation of application No. 10/677,777, filed on Oct. 3, 2003, now Pat. No. 7,470,536.

(60) Provisional application No. 60/415,818, filed on Oct. 4, 2002.

(51) Int. Cl.
*C12N 5/00* (2006.01)
*C12N 15/00* (2006.01)
*G01N 33/50* (2006.01)

(52) U.S. Cl.
CPC .................... *G01N 33/5005* (2013.01)

(58) Field of Classification Search
CPC .................................... G01N 33/5005
See application file for complete search history.

(56) References Cited

U.S. PATENT DOCUMENTS

| 5,401,629 A | 3/1995 | Harpold et al. |
| 5,436,128 A * | 7/1995 | Harpold et al. .............. 435/6.13 |
| 5,707,803 A | 1/1998 | Lamb et al. |
| 6,316,692 B1 * | 11/2001 | Readhead et al. .............. 800/14 |
| 6,383,746 B1 * | 5/2002 | Guignard et al. ............ 435/6.11 |
| 7,045,281 B2 | 5/2006 | Livelli et al. |
| 7,470,536 B2 | 12/2008 | Tovey et al. |

(Continued)

FOREIGN PATENT DOCUMENTS

| WO | WO 2004/027374 A2 | 4/2004 |
| WO | 2004039990 A2 | 5/2004 |
| WO | 2008055153 A2 | 5/2008 |

OTHER PUBLICATIONS

Berry et al (Biochemical Pharmacology, 2001. vol. 62, pp. 581-591).*

(Continued)

*Primary Examiner* — Reza Ghafoorian
(74) *Attorney, Agent, or Firm* — Browdy and Neimark, PLLC

(57) ABSTRACT

The present invention relates to a commercializable cell and to a gene reporter assay method and a kit which use this cell to determine the presence and/or the level of a molecule that activates signal transduction activity of a cell surface protein. This cell is treated in such a manner that it will have a sufficiently long shelf life for its intended purpose, whereupon at the end of its useful shelf life or at the end of its use, i.e., in an assay, the cell undergoes cellular death.

24 Claims, 12 Drawing Sheets

(56) References Cited

U.S. PATENT DOCUMENTS

| | | | |
|---|---|---|---|
| 2004/0235157 A1 | 11/2004 | Tovey et al. |
| 2005/0042643 A1 | 2/2005 | Cotter et al. |
| 2007/0099245 A1 | 5/2007 | Gorovits et al. |
| 2008/0081327 A1 | 4/2008 | Livelli et al. |
| 2008/0138818 A1 | 6/2008 | Tovey et al. |
| 2008/0248516 A1 | 10/2008 | Livelli et al. |
| 2009/0111178 A1 | 4/2009 | Tovey et al. |
| 2009/0136947 A1 | 5/2009 | Tovey et al. |

OTHER PUBLICATIONS

Wei et al (Sheng Wu Hua Xue Yu Sheng Wu Wu Li Xue Bao, Shanghai, 2001. vol. 33, No. 1, pp. 123-127, abstract).*
Eichbaum et al (J. Exp. Med. 1994, vol. 179, pp. 1985-1996).*
Kim et al. (Immunopharmacology and Immunotoxicology, 2001. vol. 23, No. 1, pp. 55-66).*
Yang et al (PNAS, 1990. vol. 87, pp. 9568-9572).*
Devireddy et al., Induction of Apoptosis by a Secreted Lipocalin That is Transcriptionally Regulated by IL-3 Deprivation, Science, Vol. 293, Aug. 3, 2001.*
Sachs et al., Control of Programmed Cell Death in Normal and Leukemic Cells: New Implications for Therapy, Blood, vol. 82, No. 1 Jul. 1, 1993: pp. 15-21.*
Limaye et al., Cryopreservation of Human Hematopoietic Cells with Membrane Stabilizers and Bioantioxidants as Additives in the Conventional Freezing Medium, Journal of Hematotherapy & Stem Cell Research 10:709-718 (2001).*
Mazur et al., Freezing of living cells: mechanisms and implications., Am J Physiol. Sep. 1984;247(3 Pt 1):C125-42.*
Lallemand et al., Constitutive expression of specific interferon isotypes in peripheral blood leukocytes from normal individuals and in promonocytic U937 cells, *Journal of Leukocyte Biology*, 60:137-146 (1996).
Canosi et al., A highly precise reporter gene bioassay for type I interferon, *Journal of Immunological Methods*, 199:69-76 (1996).
Lewis, A sensitive biological assay for interferons, *Journal of Immunological Methods*, 185:9-17 (1995).
Files et al., A novel sensitive and selective bioassay for human type I interferons, *Journal of Interferon and Cytokine Research*, 18:1019-1024 (1998).
Hammerling et al., The β-Gal interferon assay: A new, precise, and sensitive method *Journal of Interferon and Cytokine Research*, 18:451-460 (1998).
Button et al., Aequorin-expressing mammalian cell lines used to report Ca2+ mobilization, *Cell Calcium*, 14(9)663-671 (1993).
Ahern, Biochemical, reagents kits offer scientists good return on investment, *The Scientist* 9(15)20-27 (1995).
Office Action dated Apr. 7, 2006 of U.S. Appl. No. 10/677,777.
Office Action dated Sep. 7, 2007 of U.S. Appl. No. 10/677,777.
Office Action dated Mar. 19, 2008 of U.S. Appl. No. 10/677,777.
Office Action dated Oct. 16, 2009 of U.S. Appl. No. 11/765,262.
Office Action dated May 21, 2010 of U.S. Appl. No. 11/765,262.
Office Action dated Mar. 17, 2011 of U.S. Appl. No. 11/765,262.
Office Action dated Sep. 2, 2010 of U.S. Appl. No. 11/328,965.
Office Action dated Aug. 21, 2009 of U.S. Appl. No. 12/260,871.
Office Action dated Apr. 12, 2010 of U.S. Appl. No. 12/260,871.
ATCC catalog 1998.
Aschele et al., Cancer Research, 52:1855-1864 (1992).
Darnay et al., Activation of NF-κB by Rank requires tumor necrosis factor receptor-associated factor (TRAF) 6 and Nf-κB-inudcing kinase, The Journal of Biological Chemistry, 274(12):7724-7731 (1999).
Deisenhammer F, Schellekens H, Bertolotto A., Measurement of neutralizing antibodies to interferon beta in patients with multiple sclerosis, J. Neurol. (2004) 251(Suppl. 2):11:31-11:39.
Ganster et al., Complex regulation of human inducible nitric oxide synthase gene transcription by Stat 1 and NF-κB, PNAS, 98(15):8638-8643 (2001).
Farrell et al., Development and validation of luciferase reporter gene assay to measure anti-interferon beta neutralizing antibodies, Neurology, 68(12):(Suppl. 1):A117-A118 (2007).
Lleonart et al., "A novel, quantitative bioassay for type I interferon using a recombinant indicator cell line" Biotechnology 8:1263-1267(1990).
Malucchi et al., Neurology, 62(11):2031-2037 (2004).
Manna et al., IFN-alpha suppresses activation of nuclear transcription factors NF-kappa B and activator protein 1 and potentiates TNF-induced apoptosis, Journal of Immunology, 165(9)4927-4934 (2000).
Shen et al., The Journal of Biological Chemistry, 261(17):7762-7770 (1986).
Tovey et al., Characterization of neutralizing antibodies to interferons using a novel cell-based assay, Journal of Interferon and Cytokine Research, 27(8):735 (2007).
Bertolotto et al., Interferon beta neutralizing antibodies in multiple sclerosis: neutralizing activity and cross-reactivity with three different preparations, Immunopharmacology, 48:95-100 (2000).
Nagy et al., Preparing feeder cell layers from STO or mouse embryo fibroblast (MEF) cells: Treatment with γ-irradiation, Cold Spring Harb. Protoc.; 2006; doi:10.1101/pdb.prot4400.
Nagy et al., Preparing feeder cell layers from STO or mouse embryo fibroblast (MEF) cells: Treatment with mitomycin C, Cold Spring Harb. Protoc.; 2006; doi:10.1101/pdb.prot4399.
Huntsman et al., Blood Groups and Enzymes of Human Red Cells after Five Years' Storage in Liquid Nitrogen. British Medical Journal, vol. 4, 25 pp. 458-460 (1967).
Kushnaryov et al., "Ultrastructural Localization of Interferon Receptors on the Surfaces of Cultured Cells and Erythrocytes" Infection and Immunity, vol. 36, No. 2, p. 811-821 (1982).
Hodgins et al. Preservation of Trout and Salmon Erythrocytes for Blood Typing by Freezing with Dimethyl Sulphoxide. Nature, vol. 201, 28, pp. 1336-1337 (1964).
Yang et al., PNAS, 87:9568-9572 (1990).
Berry et al., Biochemical Pharmacology, 62:582-591 (2001).
Wei et al., Sheng Wu Hua Xue Yu Sheng Wu Wu Li Lue Bao, Shanghai, 33(1 ):123-127, abstract (2001).
Eichbaum et al., J. Exp. Med., 179:1985-1996 (1994).
Kim et al., Immunopharmacology and Immunotoxicology, 23(1):55-66 (2001).
Zatloukal et al., Elicitation of a systemic and protective anti-melanoma immune response by an IL-2-based vaccine, The Journal of Immunology, 3406-3419 (1995).
Lallemand et al., Reporter gene assay for the quanti!cation of the activity and neutralizing antibody response to TNFα antagonists, J. Immunol. Methods, 373:229-239 (2011).
ATCC Catalogue of Cell Lines & Hybridomas 6th Edition. 1988. American Type Culture Collection. 10 pages.
Hiscott et al., Triggering the Interferon Response: The Role of IRF-3 Transcription Factor, Journal of Interferon and Cytokine Research, 19:1-13 (1999).
Kessler et al, Two interferon-induced nuclear factors bind a single promoter element in interferon-stimulated genes, Proc. Natl. Acad. Sci. USA, 85:8521-8525 (1988).
Liu et al., ISG15 expression in response to double-stranded RNA or LPS in cultured Fetal Bovine Lung (FBL) cells, Vet Res Commun., 33:723-733 (2009).
Yang et al., Interferon Regulatory Factor-7 Synergizes with Other Transcription Factors through Multiple Interactions with p300/CBP Coactivators, The Journal of Biological Chemistry, 278:15495-15504 (2003).

* cited by examiner

SEQUENCE LISTING

```
<160> NUMBER OF SEQ ID NOS: 7

<210> SEQ ID NO 1
<211> LENGTH: 5849
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (328)..(1980)
<223> OTHER INFORMATION:

<400> SEQUENCE: 1
cccgggaggt accgagctct tacgcgtgct agctcgactc gggaaaggga aaccgaaact      60 gaagccctc gggaaaggga aaccgaaact gaagcccgat ctgcatctca attagtcagc     120
aaccatagtc ccgcccctaa ctccgcccat cccgcccta actccgccca gttccgccca     180
ttctccgccc catggctgac taatttttt tatttatgca gaggccgagg ccgcctcggc     240
ctctgagcta ttccagaagt agtgaggagg cttttttgga ggcctaggct tttgcaaaaa     300
gcttggcatt ccggtactgt tggtaaa atg gaa gac gcc aaa aac ata aag aaa     354
                                Met Glu Asp Ala Lys Asn Ile Lys Lys
                                 1               5
```

-continued

| | | |
|---|---|---|
| ggc ccg gcg cca ttc tat cct cta gag gat gga acc gct gga gag caa<br>Gly Pro Ala Pro Phe Tyr Pro Leu Glu Asp Gly Thr Ala Gly Glu Gln<br>10                           15                    20                      25 | 402 |
| ctg cat aag gct atg aag aga tac gcc ctg gtt cct gga aca att gct<br>Leu His Lys Ala Met Lys Arg Tyr Ala Leu Val Pro Gly Thr Ile Ala<br>                        30                          35                      40 | 450 |
| ttt aca gat gca cat atc gag gtg aac atc acg tac gcg gaa tac ttc<br>Phe Thr Asp Ala His Ile Glu Val Asn Ile Thr Tyr Ala Glu Tyr Phe<br>                45                        50                      55 | 498 |
| gaa atg tcc gtt cgg ttg gca gaa gct atg aaa cga tat ggg ctg aat<br>Glu Met Ser Val Arg Leu Ala Glu Ala Met Lys Arg Tyr Gly Leu Asn<br>            60                      65                      70 | 546 |
| aca aat cac aga atc gtc gta tgc agt gaa aac tct ctt caa ttc ttt<br>Thr Asn His Arg Ile Val Val Cys Ser Glu Asn Ser Leu Gln Phe Phe<br>75                          80                        85 | 594 |
| atg ccg gtg ttg ggc gcg tta ttt atc gga gtt gca gtt gcg ccc gcg<br>Met Pro Val Leu Gly Ala Leu Phe Ile Gly Val Ala Val Ala Pro Ala<br>90                          95                      100                  105 | 642 |
| aac gac att tat aat gaa cgt gaa ttg ctc aac agt atg aac att tcg<br>Asn Asp Ile Tyr Asn Glu Arg Glu Leu Leu Asn Ser Met Asn Ile Ser<br>                        110                        115                    120 | 690 |
| cag cct acc gta gtg ttt gtt tcc aaa aag ggg ttg caa aaa att ttg<br>Gln Pro Thr Val Val Phe Val Ser Lys Lys Gly Leu Gln Lys Ile Leu<br>                    125                        130                    135 | 738 |
| aac gtg caa aaa aaa tta cca ata atc cag aaa att att atc atg gat<br>Asn Val Gln Lys Lys Leu Pro Ile Ile Gln Lys Ile Ile Ile Met Asp<br>            140                      145                    150 | 786 |
| tct aaa acg gat tac cag gga ttt cag tcg atg tac acg ttc gtc aca<br>Ser Lys Thr Asp Tyr Gln Gly Phe Gln Ser Met Tyr Thr Phe Val Thr<br>155                          160                      165 | 834 |
| tct cat cta cct ccc ggt ttt aat gaa tac gat ttt gta cca gag tcc<br>Ser His Leu Pro Pro Gly Phe Asn Glu Tyr Asp Phe Val Pro Glu Ser<br>170                        175                      180                  185 | 882 |
| ttt gat cgt gac aaa aca att gca ctg ata atg aat tcc tct gga tct<br>Phe Asp Arg Asp Lys Thr Ile Ala Leu Ile Met Asn Ser Ser Gly Ser<br>                    190                        195                    200 | 930 |
| act ggg tta cct aag ggt gtg gcc ctt ccg cat aga act gcc tgc gtc<br>Thr Gly Leu Pro Lys Gly Val Ala Leu Pro His Arg Thr Ala Cys Val<br>            205                      210                    215 | 978 |
| aga ttc tcg cat gcc aga gat cct att ttt ggc aat caa atc att ccg<br>Arg Phe Ser His Ala Arg Asp Pro Ile Phe Gly Asn Gln Ile Ile Pro<br>            220                      225                    230 | 1026 |
| gat act gcg att tta agt gtt gtt cca ttc cat cac ggt ttt gga atg<br>Asp Thr Ala Ile Leu Ser Val Val Pro Phe His His Gly Phe Gly Met<br>235                          240                      245 | 1074 |
| ttt act aca ctc gga tat ttg ata tgt gga ttt cga gtc gtc tta atg<br>Phe Thr Thr Leu Gly Tyr Leu Ile Cys Gly Phe Arg Val Val Leu Met<br>250                          255                      260                  265 | 1122 |
| tat aga ttt gaa gaa gag ctg ttt tta cga tcc ctt cag gat tac aaa<br>Tyr Arg Phe Glu Glu Glu Leu Phe Leu Arg Ser Leu Gln Asp Tyr Lys<br>                    270                        275                    280 | 1170 |
| att caa agt gcg ttg cta gta cca acc cta ttt tca ttc ttc gcc aaa<br>Ile Gln Ser Ala Leu Leu Val Pro Thr Leu Phe Ser Phe Phe Ala Lys<br>                    285                        290                    295 | 1218 |
| agc act ctg att gac aaa tac gat tta tct aat tta cac gaa att gct<br>Ser Thr Leu Ile Asp Lys Tyr Asp Leu Ser Asn Leu His Glu Ile Ala<br>            300                      305                    310 | 1266 |
| tct ggg ggc gca cct ctt tcg aaa gaa gtc ggg gaa gcg gtt gca aaa<br>Ser Gly Gly Ala Pro Leu Ser Lys Glu Val Gly Glu Ala Val Ala Lys<br>315                          320                      325 | 1314 |

-continued

| | | |
|---|---|---|
| cgc ttc cat ctt cca ggg ata cga caa gga tat ggg ctc act gag act<br>Arg Phe His Leu Pro Gly Ile Arg Gln Gly Tyr Gly Leu Thr Glu Thr<br>330                    335                    340                  345 | 1362 |
| aca tca gct att ctg att aca ccc gag ggg gat gat aaa ccg ggc gcg<br>Thr Ser Ala Ile Leu Ile Thr Pro Glu Gly Asp Asp Lys Pro Gly Ala<br>                  350                    355                    360 | 1410 |
| gtc ggt aaa gtt gtt cca ttt ttt gaa gcg aag gtt gtg gat ctg gat<br>Val Gly Lys Val Val Pro Phe Phe Glu Ala Lys Val Val Asp Leu Asp<br>        365                    370                    375 | 1458 |
| acc ggg aaa acg ctg ggc gtt aat cag aga ggc gaa tta tgt gtc aga<br>Thr Gly Lys Thr Leu Gly Val Asn Gln Arg Gly Glu Leu Cys Val Arg<br>380                    385                    390 | 1506 |
| gga cct atg att atg tcc ggt tat gta aac aat ccg gaa gcg acc aac<br>Gly Pro Met Ile Met Ser Gly Tyr Val Asn Asn Pro Glu Ala Thr Asn<br>395                    400                    405 | 1554 |
| gcc ttg att gac aag gat gga tgg cta cat tct gga gac ata gct tac<br>Ala Leu Ile Asp Lys Asp Gly Trp Leu His Ser Gly Asp Ile Ala Tyr<br>410                    415                    420                  425 | 1602 |
| tgg gac gaa gac gaa cac ttc ttc ata gtt gac cgc ttg aag tct tta<br>Trp Asp Glu Asp Glu His Phe Phe Ile Val Asp Arg Leu Lys Ser Leu<br>                  430                    435                    440 | 1650 |
| att aaa tac aaa gga tat cag gtg gcc ccc gct gaa ttg gaa tcg ata<br>Ile Lys Tyr Lys Gly Tyr Gln Val Ala Pro Ala Glu Leu Glu Ser Ile<br>                    445                    450                    455 | 1698 |
| ttg tta caa cac ccc aac atc ttc gac gcg ggc gtg gca ggt ctt ccc<br>Leu Leu Gln His Pro Asn Ile Phe Asp Ala Gly Val Ala Gly Leu Pro<br>460                    465                    470 | 1746 |
| gac gat gac gcc ggt gaa ctt ccc gcc gcc gtt gtt gtt ttg gag cac<br>Asp Asp Asp Ala Gly Glu Leu Pro Ala Ala Val Val Val Leu Glu His<br>475                    480                    485 | 1794 |
| gga aag acg atg acg gaa aaa gag atc gtg gat tac gtg gcc agt caa<br>Gly Lys Thr Met Thr Glu Lys Glu Ile Val Asp Tyr Val Ala Ser Gln<br>490                    495                    500                  505 | 1842 |
| gta aca acc gcg aaa aag ttg cgc gga gga gtt gtg ttt gtg gac gaa<br>Val Thr Thr Ala Lys Lys Leu Arg Gly Gly Val Val Phe Val Asp Glu<br>                  510                    515                    520 | 1890 |
| gta ccg aaa ggt ctt acc gga aaa ctc gac gca aga aaa atc aga gag<br>Val Pro Lys Gly Leu Thr Gly Lys Leu Asp Ala Arg Lys Ile Arg Glu<br>                    525                    530                    535 | 1938 |
| atc ctc ata aag gcc aag aag ggc gga aag tcc aaa ttg taa<br>Ile Leu Ile Lys Ala Lys Lys Gly Gly Lys Ser Lys Leu<br>540                    545                    550 | 1980 |
| aatgtaactg tattcagcga tgacgaaatt cttagctatt gtaatactgc gatgagtggc | 2040 |
| agggcgggc gtaattttt taaggcagtt attggtgccc ttaaacgcct ggtgctacgc | 2100 |
| ctgaataagt gataataagc ggatgaatgg cagaaattcg ccggatcttt gtgaaggaac | 2160 |
| cttacttctg tggtgtgaca taattggaca aactacctac agagatttaa agctctaagg | 2220 |
| taaatataaa attttaagt gtataatgtg ttaaactact gattctaatt gtttgtgtat | 2280 |
| tttagattcc aacctatgga actgatgaat gggagcagtg gtggaatgcc tttaatgagg | 2340 |
| aaaacctgtt ttgctcagaa gaaatgccat ctagtgatga tgaggctact gctgactctc | 2400 |
| aacattctac tcctccaaaa aagaagagaa aggtagaaga ccccaaggac tttccttcag | 2460 |
| aattgctaag ttttttgagt catgctgtgt ttagtaatag aactcttgct tgctttgcta | 2520 |
| tttacaccac aaaggaaaaa gctgcactgc tatacaagaa aattatgaaa aatattctg | 2580 |
| taacctttat aagtaggcat aacagttata atcataacat actgtttttt cttactccac | 2640 |

```
acaggcatag agtgtctgct attaataact atgctcaaaa attgtgtacc tttagctttt    2700
taatttgtaa aggggttaat aaggaatatt tgatgtatag tgccttgact agagatcata    2760
atcagccata ccacatttgt agaggtttta cttgctttaa aaaacctccc acacctcccc    2820
ctgaacctga aacataaaat gaatgcaatt gttgttgtta acttgtttat tgcagcttat    2880
aatggttaca aataaagcaa tagcatcaca aatttcacaa ataaagcatt ttttttcactg   2940
cattctagtt gtggtttgtc caaactcatc aatgtatctt atcatgtctg gatccgtcga    3000
ccgatgccct tgagagcctt caacccagtc agctccttcc ggtgggcgcg gggcatgact    3060
atcgtcgccg cacttatgac tgtcttcttt atcatgcaac tcgtaggaca ggtgccggca    3120
gcgctcttcc gcttcctcgc tcactgactc gctgcgctcg tcgttcggc tgcggcgagc     3180
ggtatcagct cactcaaagg cggtaatacg gttatccaca gaatcagggg ataacgcagg    3240
aaagaacatg tgagcaaaag gccagcaaaa ggccaggaac cgtaaaaagg ccgcgttgct    3300
ggcgtttttc cataggctcc gcccccctga cgagcatcac aaaaatcgac gctcaagtca    3360
gaggtggcga aacccgacag gactataaag ataccaggcg tttccccctg gaagctccct    3420
cgtgcgctct cctgttccga ccctgccgct taccggatac ctgtccgcct ttctcccttc    3480
gggaagcgtg gcgctttctc aatgctcacg ctgtaggtat ctcagttcgg tgtaggtcgt    3540
tcgctccaag ctgggctgtg tgcacgaacc ccccgttcag cccgaccgct gcgccttatc    3600
cggtaactat cgtcttgagt ccaacccggt aagacacgac ttatcgccac tggcagcagc    3660
cactggtaac aggattagca gagcgaggta tgtaggcggt gctacagagt tcttgaagtg    3720
gtggcctaac tacggctaca ctagaaggac agtatttggt atctgcgctc tgctgaagcc    3780
agttaccttc ggaaaaagag ttggtagctc ttgatccggc aaacaaacca ccgctggtag    3840
cggtggtttt tttgtttgca agcagcagat tacgcgcaga aaaaaaggat ctcaagaaga    3900
tcctttgatc ttttctacgg ggtctgacgc tcagtggaac gaaaactcac gttaagggat    3960
tttggtcatg agattatcaa aaaggatctt cacctagatc cttttaaatt aaaaatgaag    4020
ttttaaatca atctaaagta tatatgagta aacttggtct gacagttacc aatgcttaat    4080
cagtgaggca cctatctcag cgatctgtct atttcgttca tccatagttg cctgactccc    4140
cgtcgtgtag ataactacga tacgggaggg cttaccatct ggccccagtg ctgcaatgat    4200
accgcgagac ccacgctcac cggctccaga tttatcagca ataaaccagc cagccggaag    4260
ggccgagcgc agaagtggtc ctgcaacttt atccgcctcc atccagtcta ttaattgttg    4320
ccgggaagct agagtaagta gttcgccagt taatagtttg cgcaacgttg ttgccattgc    4380
tacaggcatc gtggtgtcac gctcgtcgtt tggtatggct tcattcagct ccggttccca    4440
acgatcaagg cgagttacat gatcccccat gttgtgcaaa aaagcggtta gctccttcgg    4500
tcctccgatc gttgtcagaa gtaagttggc cgcagtgtta tcactcatgg ttatggcagc    4560
actgcataat tctcttactg tcatgccatc cgtaagatgc ttttctgtga ctggtgagta    4620
ctcaaccaag tcattctgag aatagtgtat gcggcgaccg agttgctctt gcccggcgtc    4680
aatacgggat aataccgcgc cacatagcag aactttaaaa gtgctcatca ttggaaaacg    4740
ttcttcgggg cgaaaactct caaggatctt accgctgttg agatccagtt cgatgtaacc    4800
cactcgtgca cccaactgat cttcagcatc ttttactttc accagcgttt ctgggtgagc    4860
aaaaacagga aggcaaaatg ccgcaaaaaa gggaataagg gcgacacgga aatgttgaat    4920
actcatactc ttcctttttc aatattattg aagcatttat cagggttatt gtctcatgag    4980
cggatacata tttgaatgta tttagaaaaa taaacaaata ggggttccgc gcacatttcc    5040
```

```
ccgaaaagtg ccacctgacg cgccctgtag cggcgcatta agcgcggcgg tgtggtggt    5100 tacgcgcagc gtgaccgcta cacttgccag cgccctagcg cccgctcctt tcgctttctt    5160
cccttccttt ctcgccacgt tcgccggctt tccccgtcaa gctctaaatc ggggctccc    5220 tttagggttc cgatttagtg ctttacggca cctcgacccc aaaaaacttg attagggtga    5280
tggttcacgt agtgggccat cgccctgata gacggttttt cgccctttga cgttggagtc    5340
cacgttcttt aatagtggac tcttgttcca aactggaaca acactcaacc ctatctcggt    5400
ctattctttt gatttataag ggattttgcc gatttcggcc tattggttaa aaaatgagct    5460
gatttaacaa aaatttaacg cgaattttaa caaaatatta cgtttacaa tttcccattc    5520 gccattcagg ctgcgcaact gttgggaagg gcgatcggtg cgggcctctt cgctattacg    5580
ccagcccaag ctaccatgat aagtaagtaa tattaaggta cgtggaggtt ttacttgctt    5640 taaaaacct cccacacctc ccctgaacc tgaaacataa aatgaatgca attgttgttg    5700
ttaacttgtt tattgcagct tataatggtt acaaataaag caatagcatc acaaatttca    5760
caaataaagc attttttttca ctgcattcta gttgtggttt gtccaaactc atcaatgtat    5820
cttatggtac tgtaactgag ctaacataa                                      5849

<210> SEQ ID NO 2
<211> LENGTH: 550
<212> TYPE: PRT
<213> ORGANISM: Artificial
<220> FEATURE:
<223> OTHER INFORMATION: Synthetic

<400> SEQUENCE: 2

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
```

```
                  210                 215                 220
Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 3
<211> LENGTH: 4412
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (358)..(1077)
<223> OTHER INFORMATION:

<400> SEQUENCE: 3
```

```
tagttattac tagcgctacc ggactcagac tcgggaaagg gaaaccgaaa ctgaagcccc    60
tcgggaaagg gaaaccgaaa ctgaagcccg atctgcatct caattagtca gcaaccatag   120
tcccgcccct aactccgccc atcccgcccc taactccgcc cagttccgcc cattctccgc   180
cccatggctg actaattttt tttatttatg cagaggccga ggccgcctcg gcctctgagc   240
tattccagaa gtagtgagga ggcttttttg gaggcctagg cttttgcaaa tctcgagctc   300
aagcttcgaa ttctgcagtc gacggtaccc cgggcccggg atccaccggt cgccacc      357
```

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 405 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | gag | ctg | gac | ggc | gac | gta | aac | ggc | cac | aag | ttc | agc | gtg | tcc | ggc | 453 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| gag | ggc | gag | ggc | gat | gcc | acc | tac | ggc | aag | ctg | acc | ctg | aag | ttc | atc | 501 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| tgc | acc | acc | ggc | aag | ctg | ccc | gtg | ccc | tgg | ccc | acc | ctc | gtg | acc | acc | 549 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| ctg | acc | tac | ggc | gtg | cag | tgc | ttc | agc | cgc | tac | ccc | gac | cac | atg | aag | 597 |
| Leu | Thr | Tyr | Gly | Val | Gln | Cys | Phe | Ser | Arg | Tyr | Pro | Asp | His | Met | Lys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cag | cac | gac | ttc | ttc | aag | tcc | gcc | atg | ccc | gaa | ggc | tac | gtc | cag | gag | 645 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| cgc | acc | atc | ttc | ttc | aag | gac | gac | ggc | aac | tac | aag | acc | cgc | gcc | gag | 693 |
| Arg | Thr | Ile | Phe | Phe | Lys | Asp | Asp | Gly | Asn | Tyr | Lys | Thr | Arg | Ala | Glu | |
| | | | | 100 | | | | | 105 | | | | | 110 | | |

| | | | | | | | | | | | | | | | | |
|---|---|---|---|---|---|---|---|---|---|---|---|---|---|---|---|---|
| gtg | aag | ttc | gag | ggc | gac | acc | ctg | gtg | aac | cgc | atc | gag | ctg | aag | ggc | 741 |
| Val | Lys | Phe | Glu | Gly | Asp | Thr | Leu | Val | Asn | Arg | Ile | Glu | Leu | Lys | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| atc | gac | ttc | aag | gag | gac | ggc | aac | atc | ctg | ggg | cac | aag | ctg | gag | tac | 789 |
| Ile | Asp | Phe | Lys | Glu | Asp | Gly | Asn | Ile | Leu | Gly | His | Lys | Leu | Glu | Tyr | |
| | | 130 | | | | | 135 | | | | | 140 | | | | |

| | | | | | | | | | | | | | | | | |
|---|---|---|---|---|---|---|---|---|---|---|---|---|---|---|---|---|
| aac | tac | aac | agc | cac | aac | gtc | tat | atc | atg | gcc | gac | aag | cag | aag | aac | 837 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | atc | aag | gtg | aac | ttc | aag | atc | cgc | cac | aac | atc | gag | gac | ggc | agc | 885 |
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| gtg | cag | ctc | gcc | gac | cac | tac | cag | cag | aac | acc | ccc | atc | ggc | gac | ggc | 933 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| ccc | gtg | ctg | ctg | ccc | gac | aac | cac | tac | ctg | agc | acc | cag | tcc | gcc | ctg | 981 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| agc | aaa | gac | ccc | aac | gag | aag | cgc | gat | cac | atg | gtc | ctg | ctg | gag | ttc | 1029 |
| Ser | Lys | Asp | Pro | Asn | Glu | Lys | Arg | Asp | His | Met | Val | Leu | Leu | Glu | Phe | |
| | | 210 | | | | | 215 | | | | | 220 | | | | |

| | | | | | | | | | | | | | | | | |
|---|---|---|---|---|---|---|---|---|---|---|---|---|---|---|---|---|
| gtg | acc | gcc | gcc | ggg | atc | act | ctc | ggc | atg | gac | gag | ctg | tac | aag | taa | 1077 |
| Val | Thr | Ala | Ala | Gly | Ile | Thr | Leu | Gly | Met | Asp | Glu | Leu | Tyr | Lys | | |
| 225 | | | | | 230 | | | | | 235 | | | | | | |

```
agcggccgcg actctagatc ataatcagcc ataccacatt tgtagaggtt ttacttgctt   1137
taaaaaacct cccacacctc ccctgaacc tgaaacataa aatgaatgca attgttgttg    1197
ttaacttgtt tattgcagct tataatggtt acaaataaag caatagcatc acaaatttca   1257
caaataaagc attttttca ctgcattcta gttgtggttt gtccaaactc atcaatgtat    1317
```

```
cttaaggcgt aaattgtaag cgttaatatt ttgttaaaat tcgcgttaaa tttttgttaa      1377
atcagctcat ttttaacca ataggccgaa atcggcaaaa tcccttataa atcaaaagaa      1437
tagaccgaga tagggttgag tgttgttcca gtttggaaca agagtccact attaaagaac      1497
gtggactcca acgtcaaagg gcgaaaaacc gtctatcagg gcgatggccc actacgtgaa      1557
ccatcaccct aatcaagttt tttggggtcg aggtgccgta aagcactaaa tcggaaccct      1617
aaagggagcc cccgatttag agcttgacgg ggaaagccgg cgaacgtggc gagaaaggaa      1677
gggaagaaag cgaaaggagc gggcgctagg gcgctggcaa gtgtagcggt cacgctgcgc      1737
gtaaccacca caccgccgc gcttaatgcg ccgctacagg gcgcgtcagg tggcactttt       1797
cggggaaatg tgcgcggaac ccctatttgt ttatttttct aaatacattc aaatatgtat      1857
ccgctcatga caataaacc ctgataaatg cttcaataat attgaaaaag gaagagtcct       1917
gaggcggaaa gaaccagctg tggaatgtgt gtcagttagg gtgtggaaag tccccaggct      1977
ccccagcagg cagaagtatg caaagcatgc atctcaatta gtcagcaacc aggtgtggaa      2037
agtccccagg ctccccagca ggcagaagta tgcaaagcat gcatctcaat tagtcagcaa      2097
ccatagtccc gcccctaact ccgcccatcc cgcccctaac tccgcccagt ccgcccatt       2157
ctccgcccca tggctgacta attttttta tttatgcaga ggccgaggcc gcctcggcct       2217
ctgagctatt ccagaagtag tgaggaggct ttttggagg cctaggcttt tgcaaagatc       2277
gatcaagaga caggatgagg atcgtttcgc atgattgaac aagatggatt gcacgcaggt      2337
tctccggccg cttgggtgga gaggctattc ggctatgact gggcacaaca gacaatcggc      2397
tgctctgatg ccgccgtgtt ccggctgtca gcgcagggc gcccggttct ttttgtcaag      2457
accgacctgt ccggtgccct gaatgaactg caagacgagg cagcgcggct atcgtggctg      2517
gccacgacgg gcgttccttg cgcagctgtg ctcgacgttg tcactgaagc gggaagggac      2577
tggctgctat tgggcgaagt gccggggcag gatctcctgt catctcacct tgctcctgcc      2637
gagaaagtat ccatcatggc tgatgcaatg cggcggctgc atacgcttga tccggctacc      2697
tgcccattcg accaccaagc gaaacatcgc atcgagcgag cacgtactcg gatggaagcc      2757
ggtcttgtcg atcaggatga tctggacgaa gagcatcagg ggctcgcgcc agccgaactg      2817
ttcgccaggc tcaaggcgag catgcccgac ggcgaggatc tcgtcgtgac ccatggcgat      2877
gcctgcttgc cgaatatcat ggtggaaaat ggccgctttt ctggattcat cgactgtggc      2937
cggctgggtg tggcggaccg ctatcaggac atagcgttgg ctacccgtga tattgctgaa      2997
gagcttggcg gcgaatgggc tgaccgcttc ctcgtgcttt acggtatcgc cgctcccgat      3057
tcgcagcgca tcgccttcta tcgccttctt gacgagttct tctgagcggg actctggggt      3117
tcgaaatgac cgaccaagcg acgcccaacc tgccatcacg agatttcgat tccaccgccg      3177
ccttctatga aaggttgggc ttcggaatcg ttttccggga cgccggctgg atgatcctcc      3237
agcgcgggga tctcatgctg gagttcttcg cccaccctag gggaggcta actgaaacac       3297
ggaaggagac aataccggaa ggaacccgcg ctatgacggc aataaaaaga cagaataaaa      3357
cgcacggtgt tgggtcgttt gttcataaac gcggggttcg tcccagggc tggcactctg       3417
tcgataccc accgagaccc cattggggcc aatacgcccg cgtttcttcc ttttccccac       3477
ccaccccc aagttcgggt gaaggcccag ggctcgcagc caacgtcggg gcggcaggcc        3537
ctgccatagc ctcaggttac tcatatatac tttagattga tttaaaactt cattttaat      3597
ttaaaaggat ctaggtgaag atcctttttg ataatctcat gaccaaaatc ccttaacgtg      3657
```

```
agttttcgtt ccactgagcg tcagaccccg tagaaaagat caaaggatct tcttgagatc   3717 cttttttttct gcgcgtaatc tgctgcttgc aaacaaaaaa accaccgcta ccagcggtgg   3777
tttgtttgcc ggatcaagag ctaccaactc ttttttccgaa ggtaactggc ttcagcagag   3837
cgcagatacc aaatactgtc cttctagtgt agccgtagtt aggccaccac ttcaagaact   3897
ctgtagcacc gcctacatac ctcgctctgc taatcctgtt accagtggct gctgccagtg   3957
gcgataagtc gtgtcttacc gggttggact caagacgata gttaccggat aaggcgcagc   4017
ggtcgggctg aacggggggt tcgtgcacac agcccagctt ggagcgaacg acctacaccg   4077
aactgagata cctacagcgt gagctatgag aaagcgccac gcttcccgaa gggagaaagg   4137
cggacaggta tccggtaagc ggcagggtcg aacaggaga gcgcacgagg gagcttccag   4197
ggggaaacgc ctggtatctt tatagtcctg tcgggtttcg ccacctctga cttgagcgtc   4257
gatttttgtg atgctcgtca gggggggcgga gcctatggaa aaacgccagc aacgcggcct   4317
ttttacggtt cctggccttt tgctggcctt ttgctcacat gttctttcct gcgttatccc   4377
ctgattctgt ggataaccgt attaccgcca tgcat                              4412
```

<210> SEQ ID NO 4
<211> LENGTH: 239
<212> TYPE: PRT
<213> ORGANISM: Artificial
<220> FEATURE:
<223> OTHER INFORMATION: Synthetic

<400> SEQUENCE: 4

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
```

```
<210> SEQ ID NO 5
<211> LENGTH: 60
<212> TYPE: DNA
<213> ORGANISM: Artificial
<220> FEATURE:
<223> OTHER INFORMATION: Synthetic

<400> SEQUENCE: 5
ctcgggaaag ggaaaccgaa actgaagccc ctcgggaaag ggaaaccgaa actgaagccc    60

<210> SEQ ID NO 6
<211> LENGTH: 15
<212> TYPE: DNA
<213> ORGANISM: Artificial
<220> FEATURE:
<223> OTHER INFORMATION: Synthetic

<400> SEQUENCE: 6
ggraaagwga aactg                                                    15

<210> SEQ ID NO 7
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is either a, c, g, or t.
<220> FEATURE:
<221> NAME/KEY: misc_feature
<222> LOCATION: (6)..(6)
<223> OTHER INFORMATION: n is either a, c, g, or t.
<220> FEATURE:
<221> NAME/KEY: misc_feature
<222> LOCATION: (16)..(16)
<223> OTHER INFORMATION: n is either a, c, g, or t.
<220> FEATURE:
<221> NAME/KEY: misc_feature
<222> LOCATION: (19)..(19)
<223> OTHER INFORMATION: n is either a, c, g, or t.
<220> FEATURE:
<221> NAME/KEY: misc_feature
<222> LOCATION: (21)..(21)
<223> OTHER INFORMATION: n is either a, c, g, or t.

<400> SEQUENCE: 7
nnnsanttcc gggaantgns n                                             21
```

GENE REPORTER ASSAY, KIT, AND CELLS FOR DETERMINING THE PRESENCE AND/OR THE LEVEL OF A MOLECULE THAT ACTIVATES SIGNAL TRANSDUCTION ACTIVITY OF A CELL SURFACE PROTEIN

CROSS-REFERENCE TO RELATED APPLICATIONS

This application is a continuation of application Ser. No. 10/677,777, filed Oct. 3, 2003, which claims the benefit of priority from U.S. provisional application No. 60/415,818, filed Oct. 4, 2002, the entire contents of which are herein incorporated by reference.

BACKGROUND OF THE INVENTION

1. Field of the Invention

The present invention relates to a gene reporter assay and a kit for determining the presence and/or the level in a sample of a molecule that activates the signal transduction activity of a cell surface protein. The present invention further relates to a cell which can be used in such an assay and to a method for preparing such a cell.

2. Description of the Related Art

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as cytokines, growth factors, hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. Other extracellular signal molecules cause activation of latent cytoplasmic signal transducers and activators of transcription (STAT) protein that enhance the transcription of specific sets of genes.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell Surface Receptors

Cell surface-localized receptors are membrane spanning proteins that bind extracellular signalling molecules or changes in the extracellular environment and transmit the signal via signal transduction pathways to effect a cellular response. Cell surface receptors bind circulating signal molecules, such as cytokines, growth factors and hormones, etc., as the initiating step in the induction of numerous intracellular pathways. Receptors are classified on a structural basis or on the basis of the particular type of pathway that is induced. Among these classes of receptors are classes of cytokine receptors which include those that bind growth factors and have intrinsic tyrosine kinase activity, such as the heparin binding growth factor (HBGF) receptors, the immunoglobulin receptor superfamily, the hematopoietin/cytokine receptor superfamily, the nerve-growth factor receptor superfamily, other receptor tyrosine or serine kinases, and those that couple to effector proteins through guanine nucleotide binding regulatory proteins, which are referred to as G protein coupled receptors and G proteins, respectively.

Cytokines are intercellular messengers which coordinate communication between cells within a particular tissue, for example, antibody and T cell immune system interactions, and serve to modulate or modify the biological response. They are pleiotropic and have a broad spectrum of biological effects on more than one type of cell or tissue. The receptors for cytokines are broadly grouped into two classes, where the Class I cytokine receptors include receptors that bind various interleukins (IL-2, IL-3, IL-4, IL-6, IL-7, IL-9, IL-11, IL-12, IL-15), erythropoietin (EPO), growth hormone (GH), granulocyte colony stimulating factor (G-CSF), granulocyte macrophage colony stimulating factor (GM-CSF), leukemia inhibitory factor (LIF), and ciliary neurotrophic factor (CNTF), and the Class II cytokine receptors include receptors that bind interferon (IFN) $\alpha/\beta$, IFN$\gamma$, and IL-10.

Interferon Receptors

Human interferons (IFNs) are a family of homologous helical cytokines composed of four distinct species: $\alpha$, $\beta$, $\gamma$ and $\omega$ based on nucleotide and amino acid sequence homology. The Type I IFNs, $\alpha$, $\beta$, and $\omega$, are encoded by at least 12 functional IFN$\alpha$ genes, an IFN$\omega$ gene, and a more distantly related IFN$\beta$ gene. Type II IFN, or IFN$\gamma$, is encoded by an unrelated gene and binds to a distinct cell surface receptor (De Maeyer et al., 1988; Pestka et al., 1987 and Diaz et al., 1993).

Type I IFNs bind to a common receptor, as shown by their ability to cross-compete for receptor binding (Pestka et al., 1987; Branca et al., 1981; and Merlin et al., 1985). The Type 1 interferon receptor has the largest number of natural ligands, some 14 in all, of all known cytokine receptors. Binding of interferons to their cell surface receptor represents the initial and probably most specific step in the IFN signaling pathway.

The Type I IFN receptor is composed of two transmembrane glycoproteins, IFNAR1 and IFNAR2 (Uze et al., 1990; Novick et al., 1994; Lutfalla et al., 1995; Domanski et al., 1995), which are rapidly tyrosine-phosphorylated following IFN binding (Platanias et al., 1994; Constantinescu et al., 1994; and Abramovich et al., 1994). Both subunits belong to the class II cytokine receptor superfamily (Bazan et al., 1990 and Thoreau et al., 1990) and are required for high affinity ligand binding and the establishment of biological activity (Langer et al., 1996 and Domanski et al., 1996). Class II cytokine receptors are distinguished from Class I receptors on the basis of the pattern of the conserved pairs of cysteine residues that are thought to form disulfide bonds.

In contrast to other cytokine receptors, particularly the IFN-$\gamma$ receptor, neither IFNAR1 nor IFNAR2 alone bind to IFN$\alpha$ or IFN$\beta$ with an affinity comparable to the heterodimer. Despite the fact that IFNAR2 plays a prominent role in ligand binding, IFNAR1 contributes to IFN binding by increasing the affinity of the receptor complex (4-10 fold) relative to that of IFNAR2 alone. IFNAR1 also modulates the specificity of ligand binding relative to that observed with IFNAR2 alone (Cohen et al., 1995; Russell-Harde et al., 1995; Cutrone et al., 1997; and Cook et al., 1996). IFNAR1 has a larger extracellular domain than most other class II cytokine receptors, composed of 4 immunoglobulin-like subdomains separated by di- or tri-proline motifs which can be divided into two tandem repeats (Novick et al., 1994; Lutfalla et al., 1992; and Uzé et al., 1995).

Human, murine and bovine IFNAR1 have been cloned and expressed in human and murine cells. Studies performed with transfected cells show that IFNAR1 plays a central role in ligand binding, cellular responses to IFNs and in the induction of the biological activities of the Type I interferons (Novick et al., 1994; Abramovich et al., 1994; Uzé et al., 1992; Mouchel-Vielh et al., 1992; Lim et al., 1993; Cleary et al., 1994; Constantinescu et al., 1995; Hwang et al., 1995; Vandenbroek et al., 1995; and Colamonici et al., 1994). Furthermore, the intracellular domain of IFNAR1 has been shown to play a key role in the transduction of the signal initiated at the cell surface by binding of Type I interferons to the nucleus (Basu et al., 1998). Targeted disruption of the IFNAR1 gene results in the loss of the antiviral response to Type I IFNs demonstrating that this receptor polypeptide is an essential component of the receptor complex and that both IFNAR1 and IFNAR2 subunits are required for IFNα and IFNβ signaling (Vandenbroek et al., 1995; Muller et al., 1994; Fiette et al., 1995; Steinhoff et al., 1995; and van den Broek et al., 1995).

Binding of type I interferon to the receptor complex activates two Janus kinases, Tyk2 and JAK1, which mediate the tyrosine phosphorylation and activation of two latent cytoplasmic transcription factors STAT1 and STAT2 which form a complex with a p48 DNA binding protein, interferon responsive protein 9 (IRF 9), which is translocated to the nucleus to promote specific gene transcription (Fu et al., 1992; Schindler et al., 1992; Darnell et al., 1994; Ihle et al, 1995; and Taniguchi, 1995). Both Tyk2 and STAT2 are constitutively associated with the membrane proximal region of the IFNAR1 chain, while JAK1 and STAT1 are physically associated with IFNAR2 and all four factors are rapidly activated during IFNα stimulation (Lutfalla et al., 1995; Bazan, 1990; Basu et al., 1998; Barbieri et al., 1994; Velazquez et al., 1995; Uddin et al., 1995; Yan et al., 1996(a) and 1996(b).

G-Coupled Receptors

The G protein transmembrane signaling pathways consist of three proteins: receptors, G proteins and effectors. G proteins, which are the intermediaries in transmembrane signaling pathways, are heterodimers and consist of α, β and γ subunits. Among the members of a family of G proteins the α subunits differ. Functions of G proteins are regulated by the cyclic association of GTP with the α subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

Growth Factors and Growth Factor Receptors

Polypeptide growth factors are modulators of cell proliferation and differentiation whose biological functions are mediated by the interaction of the growth factor with cell surface receptors and subsequent alterations in gene expression. Growth factors bind to specific receptors and appear to induce tyrosine phosphorylation and c-fos mRNA synthesis. In addition, at least some growth factors, such as platelet-derived growth factor (Yeh et al., 1987) and heparin-binding growth factor-2 or basic fibroblast growth factor (Bouche et al., 1987), are translocated to the nucleus.

Activation of growth factor receptors by interaction with specific growth factors or with agents such as phorbol mistric acetate (PMA) activates protein kinase C, which is a family of phospholipid- and calcium-activated protein kinases. This activation results in the transcription of an array of proto-oncogene transcription factor encoding genes, including c-fos, c-myc and c-jun, proteases, protease inhibitors, including collagenase type I and plasminogen activator inhibitor, and adhesion molecules, including intercellular adhesion molecule I. Protein kinase C activation antagonizes growth factor activity by the rapid phosphorylation of growth factor receptors, which thereby decreases tyrosine kinase activity. Growth factors and other mitogens that induce cell proliferation and cell growth are believed to play a role in tumor growth, which often carry identifiable cell surface receptors specific for growth factors and other extracellular signals.

The interaction of nerve growth factor (NGF) with its receptor is typical of the array of responses such an extracellular signal induces. NGF is a polypeptide growth hormone that is necessary for differentiation and growth of the neural crest-derived sensory neuron. NGF binds to its specific cell surface receptor and is retrogradely transported to the cell body (Changelian et al., 1989). This initiates a cascade of intracellular events, culminating in a differentiated phenotype. PC12 cells, which are a rat pheochromocytoma cell line, are used as a model for the study of NGF-mediated differentiation. When treated with NGF, PC12 cells change from replicating adrenal-chromaffin-like cells to nonreplicating, electrically excitable sympathetic-neuron-like cells.

Concomitant with the phenotypic changes, there is induction and expression of specific genes. Binding of NGF to PC12 cells induces the immediate and rapid expression of certain genes, including the c-fos, NGF1-A and NGF1-B genes, which are referred to as early genes. Such early genes are believed to encode transcriptional regulators. The NGF-1A gene product contains tandemly repeated "zinc finger" domains that are characteristic of DNA-binding proteins, and the NGF1-B protein is homologous to members of the glucocorticoid receptor family and, thus, may function as a ligand-dependent modulator of transcription. The c-fos gene product, FOS appears to function as a transcriptional regulatory molecule.

The C-Fos Gene and Related Genes

As discussed above, induction of expression of the c-fos gene is an event that is common to a number of response pathways that are initiated by the activity of a variety of cell surface proteins.

The c-fos gene product, FOS, associates with the transcription activator JUN, which is the product of the c-jun gene, to form a complex that forms a transcription activation complex, AP-1. Transcription of both c-fos and c-jun is induced rapidly and transiently following stimulation. The induced mRNAs accumulate for 1-2 hours in the cytoplasm where the FOS and JUN proteins, which are short-lived, are translated and then translocated to the nucleus to form a heterodimeric protein complex that binds to the DNA regulatory element, AP-1 binding site.

The c-fos and c-jun genes are members of gene families that encode proteins that participate in the formation of heterodimeric complexes that interact with AP-1 binding sites.

Transcription factor AP-1 is composed of several protein complexes whose concentrations change upon cell stimulation. These complexes specifically interact with a seven-base core nucleotide sequence motif, that is known to be a relatively common constituent of both positive and negative transcriptional regulatory elements and that is required for both basal and induced levels of gene expression.

The gene products, FOS and JUN cooperate in the regulation of target genes that underlie many cellular and adaptive responses to the environment. They are involved in a number of neurophysiological processes.

Thus, c-fos induction involves distinct second messenger pathways that act via separate regulatory elements and that differentially modify, the resulting gene product, FOS, which in turn interacts in different ways with differentially modified JUN protein. Therefore, a multitude of extracellular events induce expression of a small number of inducible proteins that form an array of protein complexes that can differentially bind to DNA regulatory elements that contain AP-1 binding sites. Therefore, numerous cell surface proteins can act via overlapping transduction pathways and transduce extracellular signals that ultimately induce a variety of responses.

There are many assays that may rely on in vivo activity in a living cell line. One example is a cell line having an Interferon Stimulatory Response Element (ISRE) connected to a luciferase gene, or another reporter gene, so that when the cell line is subjected to the presence of interferon as an extracellular signal, the signal transduction activity of endogenous interferon cell surface receptors produces a signal that activates the ISRE, which then causes transcription of the luciferase gene. Thus, the activity of luciferase in creating light can be measured and is related to the amount of interferon which is present in the sample, and which is proportional to the amount of interferon over a particular range (Lallemand et al., 1996).

Lleonart et al. (1990) described a reporter gene assay for Type I interferon based on monkey Vero cells transfected with Type I interferon inducible mouse Mx promoter linked to the human growth hormone (hGH) gene as the reporter gene. This Type I interferon assay was developed further by transfecting monkey Vero cells with a plasmid carrying the luciferase reporter gene under the control of the Type I interferon inducible mouse Mxl promoter (Canosi et al., 1996).

A further type of interferon reporter gene assay was developed by Hammerling et al. (1998) who used a human glioblastoma cell line transfected with a reporter gene construct of glial fibrillary acidic protein (GFAP) promoter and an *E. coli* β-galactosidase (lacZ) reporter gene. In this particular assay, it is the reduction/inhibition of β-galactosidase expression by either human Type I or Type II interferon in a selective and dose dependent manner that is measured.

With the types of cell lines which can be used in such assays, there is a problem in commercializing them in that once the cell line is shipped for use in a single assay, the end user can grow the cells and then use their own stock of such cells for future assays without the need to order more cells from the supplier.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to develop a way to make a desirable cell line an essentially "one time use" commercial cell line with a sufficiently long shelf life for its intended purpose so that whenever a user uses this commercial cell line, such as in an assay, this user must purchase cells of this commercial cell line from a supplier.

Thus, the present invention provides a cell transformed with a reporter gene construct in which the expression of the reporter gene product is regulated by the signal transduction activity of a cell surface protein in response to an extracellular signal. This cell according to the present invention has been treated so that it will maintain signal transduction activity for at least about 1 hour, but no more than 30 days at a temperature above freezing, before losing that ability. Such a treated cell has acquired the commercial advantage of having a sufficiently long shelf life for its purpose by maintaining the cell in a state or by inhibiting cell division, whereupon at the end of its useful shelf life or at the end of its use the cell undergoes cellular death such as by apoptosis.

The present invention also provides a cell based assay kit for determining the level in a sample of a molecule that activates the signal transduction activity of a cell surface protein. Such a kit includes a testing device with multiple wells and a reagent containing a plurality of the cell of the present invention.

Further provided by the present invention is a method for preparing the cell of the present invention, which loses signal transduction within 30 days. This method involves transforming a host cell with a reporter gene construct described above for the cell of the present invention and then treating the transformed cell so that the treated transformed cell will maintain signal transduction activity for at least about 1 hour but no more than about 30 days at a temperature above freezing before losing the signal transduction activity.

Another aspect of the present invention is directed to a method for determining the presence and/or the level in a sample of a molecule that activates the signal transduction activity of a cell surface protein.

with 1.0 µg/ml of vinblastine, centrifuged, and suspended of RPMI 1640 medium with 40% FBS, 10% glycerol, and 2.5% DMSO. The cells were then distributed into each well of a micro-titer culture plate ($2\times10^5$ cells in 25 µl/well) or added to a cryo-preservation ampoule ($2\times10^7$ cells in 1.0 ml) and frozen at $-80°$ C. After storage at $-80°$ C. and subsequent storage at $-20°$ C., the micro-titer plate and cryo-preservation ampoule were thawed rapidly and a standard preparation of human IFN α was titrated in the micro-titer plate, or the contents of the cryo-preservation ampoule ($2\times10^7$ cells in 1.0 ml) were diluted in 6.5 ml of RPMI 1640 medium and 75 µl of cell suspension was then distributed into each well of a micro-titer culture plate and a standard preparation of human IFN α was titrated in the micro-titer plate in the luciferase gene reporter assay procedure described above.

Figure 24:
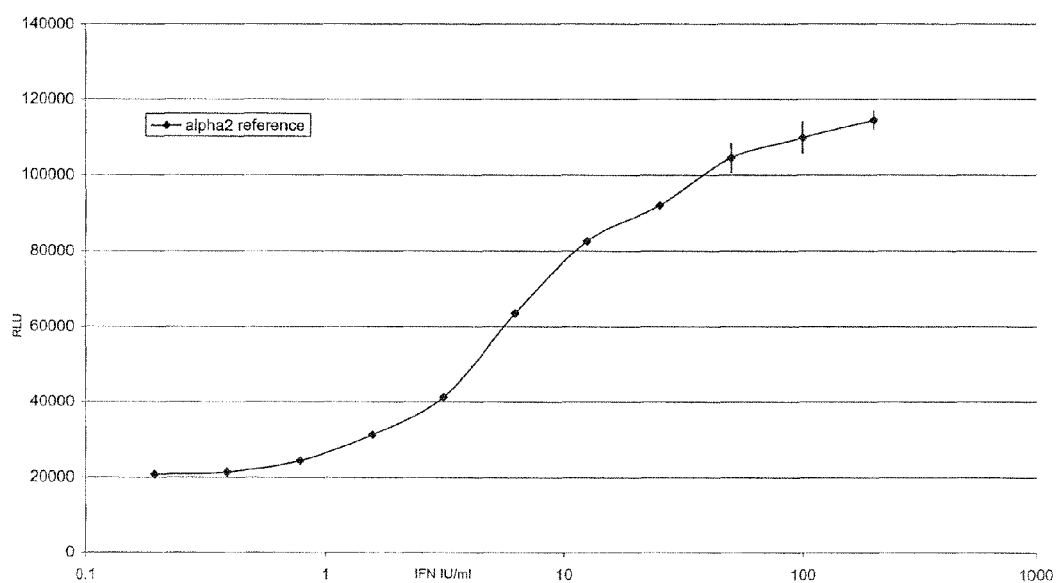

FIG. 24 is a graph showing the titration of a standard interferon preparation on PIL5 cells following freezing. PIL5 cells were treated for 10 minutes at $37°$ C. with 1.0 µg/ml of vinblastine, centrifuged, and suspended at a concentration of $2\times10^5$ cells/25 µl in RPMI 1640 medium with 40% FBS, 10% glycerol, and 2.5% DMSO, and distributed into each well of a micro-titer culture plate and frozen at $-80°$ C. After storage at $-80°$ C. and subsequent storage at $-20°$ C., the plate was thawed rapidly and a standard preparation of human IFN α was titrated in the luciferase gene reporter assay procedure described above.

DETAILED DESCRIPTION OF THE INVENTION

The present invention is directed to a cell transformed with a reporter gene construct comprising a nucleotide sequence encoding a reporter gene product operatively linked to one or more transcriptional control elements that is regulated by the signal transduction activity of a cell surface protein in response to an extracellular signal. This cell of the present invention has been treated in such a way that it will maintain the signal transduction activity of the cell surface protein for at least about 1 hour but no more than about 30 days at a temperature above freezing before losing the signal transduction activity. Thus, not only does the cell of the present invention have a sufficient shelf life by inhibiting cell division or by maintaining the cell in a frozen state for the purpose desired by an end user, such as for conducting an assay, but it has been treated in such a manner that the cells can be frozen, or even kept at room temperature, allowing storage for extended periods and transportation in a frozen state or at room temperature. The cell of the present invention also has the commercial advantage to a supplier of being a one time use cell that cannot be propagated by the end user for possible further use. Instead, the cell, preferably as part of a kit, must be purchased from the supplier for each single use.

The cell according to the present invention may be any eukaryotic or prokaryotic cell. Mammalian and avian cells are however preferred, with human cells most preferred. Non-limiting examples of other suitable cells include other vertebrate cells, plant protoplasts, fungal and yeast cells, and bacterial cells.

The cell surface protein from which its signal transduction activity, in response to an extracellular signal, regulates the expression of a reporter gene product can be any cell surface protein that is known to those of skill in the art or that may be identified by those of skill in the art. Exemplary cell surface proteins include, but are not limited to, cell surface receptors and ion channels. Non-limiting examples of cell surface receptors include cytokine receptors (e.g., receptors for Type I interferon, Type II interferon, interleukins, growth hormone, erythropoietin (EPO), granulocyte colony stimulating factor (G-CSF), granulocyte macrophage colony stimulating factor (GM-CSF), leukemia inhibitory factor (LIF), ciliary neurotrophic factor (CNTF), etc.), growth factor receptors, hormone receptors, T cell receptors, antigen receptors, complement receptors, and neuroreceptors. The reference text, J. M. Cruse and Robert E. Lewis, *Atlas of Immunology*, CRC Press, Washington, D.C., 1999, which discloses many receptors involved in immune response and immune system interactions is entirely incorporated herein by reference. Cell surface receptors also include, but are not limited to, muscarinic receptors (e.g., human M2 (GenBank accession #M16404); rat M3 (GenBank accession #M16407); human M4 (GenBank accession #M16405); human M5 (Bonner et al., 1988); and the like); neuronal nicotinic acetylcholine receptors (e.g., the α2, α3 and β2 subtypes); the rat α2 subunit (Wada et al., 1988); the rat α3 subunit (Boulter et al., 1986); the rat α4 subunit (Goldman et al., 1987); the rat α5 subunit (Boulter et al., 1990); the rat β2 subunit (Deneris et al., 1988); the rat β3 subunit (Deneris et al., 1989); the rat β4 subunit (Duvoisin et al., 1989); combinations of the rat α subunits, β subunits and α and β subunits; GABA receptors (e.g., the bovine α1 and β1 subunits (Schofield et al., 1987); the bovine α2 and α3 subunits (Levitan et al., 1988); the γ-subunit (Pritchett et al., 1989); the β2 and β3 subunits (Ymer et al., 1989); the δ subunit (Shivers, B. D., 1989); and the like); glutamate receptors (e.g., receptor isolated from rat brain (Hollmann et al., 1989); and the like); adrenergic receptors (e.g., human β1 (Frielle et al., 1987); human α2 (Kobilka et al., 1987); hamster β2 (Dixon et al., 1986); and the like); dopamine receptors (e.g., human D2 (Stormann et al., 1990); rat (Bunzow et al., 1988); and the like); NGF receptors (e.g., human NGF receptors (Johnson et al., 1986); and the like); serotonin receptors (e.g., human 5HT1a (Kobilka et al., 1987); rat 5HT2 (Julius et al., 1990); rat 5HT1c (Julius et al., 1988); and the like).

Ion channels include, but are not limited to, calcium ion channels (e.g., human neuronal α2 subunit (see WO89/09834); rabbit skeletal muscle a1 subunit (Tanabe et al. 1987); rabbit skeletal muscle α2 subunit (Ellis et al., 1988); rabbit skeletal muscle β subunit (Ruth et al., 1989); rabbit skeletal muscle γ subunit (Jay et al., 1990); and the like); potassium ion channels (e.g., rat brain (BK2) (McKinnon, D., 1989); mouse brain (BK1) (Tempel et al., 1988); and the like); sodium ion channels (e.g., rat brain I and II (Noda et al., 1986); rat brain III (Kayano et al., 1988); and others).

It will be appreciated by those of skill in the art that the cell surface protein discussed above is preferably endogenous to the cell of the present invention. However, it will also be appreciated that the cell surface protein may be expressed from cloned DNA, such as to supplement the number of the cell surface protein at the surface of the cell, or the cell surface protein may be expressed from cloned DNA but is a cell surface protein that is heterologous to the host cell.

For signal transduction, the intracellular signal that is transduced is initiated by the specific interaction of an extracellular signal, i.e., a molecule or a change in environment, with a receptor or ion channel present on the cell surface. This interaction sets in motion a cascade of intracellular events, the ultimate consequence of which is a rapid and detectable change in the expression of a gene product, which in the cell of the present invention is a reporter gene product. The extracellular signal or effector molecule is any compound or substance that in some manner specifically alters the activity of a cell surface protein. Examples of such signals include, but are not limited to, molecules such as cytokines (i.e., interferons), growth factors, hormones, endorphins, neurotransmitters, acetylcholine, and mitogenic substances, such as phorbol mistric acetate (PMA), that bind to cell surface receptors and ion channels and modulate the activity of such receptors and channels. For example, antagonists are extracellular signals that block or decrease the activity of cell surface protein and agonists are examples of extracellular signals that potentiate, induce or otherwise enhance the activity of cell surface proteins.

The reporter gene construct carried by the cell of the present invention is a DNA molecule that includes a nucleotide sequence encoding a reporter gene product operatively linked to transcriptional control elements/sequences. Transcription of the reporter gene is controlled by these sequences. The activity of at least one or more of these control sequences is directly or indirectly regulated by the cell surface protein. The transcriptional control sequences include but are not limited to promoters and other regulatory regions, such as enhancer sequences and repressor and activator binding sites, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product expressed.

A promoter that is regulated or mediated by the activity of a cell surface protein is a promoter whose activity changes when a cell is exposed to a particular extracellular signal by virtue of the presence of cell surface proteins whose activities are affected by the extracellular signal. For example, the c-fos promoter is specifically activated upon the specific interaction of certain extracellular signals, such as growth hormones, with a cell surface protein, such as a growth hormone receptor. In particular, the regulation of such promoters by the cell surface protein, though indirect, occurs within minutes of the interaction of the cell surface protein with the extracellular signal. As used herein, operative linkage refers to the linkage of a transcriptional control element, i.e., promoter, to a nucleotide coding sequence such that the transcriptional control element is properly positioned for its activity of binding RNA polymerase and initiating transcription of the nucleotide coding sequence. Thus, a nucleotide coding sequence in operative linkage with a promoter is downstream, with respect to the direction of transcription, from the promoter, is in the correct reading frame with respect to the transcription initiation site and is inserted in a manner such that transcription elongation proceeds through the nucleotide coding sequence.

Suitable transcriptional control elements may be obtained or derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (Sheng et al., 1990), such as c-fos. Immediate early genes are genes that are rapidly induced upon binding of a ligand to a cell surface protein. The transcriptional control elements that are preferred for use in the reporter gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Suitable promoters and transcriptional control elements include, but are not limited to, the vasoactive intestinal peptide (VIP) gene promoter (cAMP responsive; Fink et al., 1988); the somatostatin gene promoter (cAMP responsive; Montminy et al., 1986); the proenkephalin promoter (responsive to cAMP, nicotinic agonists, and phorbol esters; Comb et al. 1986); the phosphoenolpyruvate carboxy-kinase gene promoter (cAMP responsive; Short et al., 1986); the NGFI-A gene promoter (responsive to NGF, cAMP, and serum; Changelian et al., 1989); the transcriptional control elements obtained or derived from the c-fos gene; and others that may be known to or prepared by those of skill in the art.

The c-fos proto oncogene is the cellular homologue of the transforming gene of FBJ osteosarcoma virus. It encodes a nuclear protein that is most likely involved in normal cellular growth and differentiation. Transcription of c-fos is transiently and rapidly activated by growth factors and by inducers of other cell surface proteins, including hormones, differentiation-specific agents, stress, mitogens and other known inducers of cell surface proteins. Activation is protein synthesis independent. The c-fos regulatory elements include a TATA box that is required for transcription initiation, two upstream elements for basal transcription, and an enhancer, which includes an element with dyad symmetry and which is required for induction by TPA, serum, EGF, and PMA. The 20 bp transcriptional enhancer element located between −317 and −298 bp upstream from the c-fos mRNA cap site, which is essential for serum induction in serum starved NIH 3T3 cells. One of the two upstream elements is located at −63 to −57 and it resembles the consensus sequence for cAMP regulation.

Transcriptional control elements, particularly as they relate to a preferred embodiment of the present invention where Type I and/or Type II interferon is the extracellular signal, are preferably an interferon stimulatory response element (ISRE) and/or a gamma activated sequence (GAS). There are a number of ISREs characterized from different human genes responsive to Type I interferon and a consensus sequence, ggr aaagwGAAActg (SEQ ID NO:6; capital letters denote core sequence; underlines denote high conservation), to which the STAT1/STAT2/IRF9 complex binds, was identified for ISRE (Levy et al., 1988). A preferred ISRE is from the human ISG15 gene and is presented as SEQ ID NO:5 where nucleotides 41-55 correspond to the consensus ISRE sequence. ISRE is also highly conserved among species. For example, a sequence present in the promoter region of the interferon inducible chicken Mx gene (Schumacher et al., 1994) is similar to that found in primates and conforms to the ISRE consensus sequence for mammalian interferon responsive genes including rodents and cows (see FIG. 2 of Perry et al., 1999).

Regarding GAS, to which the STAT1 homodimer binds in genes responsive to Type II interferon, a consensus sequence, nnnsanttccgGGAAntgnsn (SEQ ID NO:7; capital letters denote core sequence; underlines denote high conservation), from many selected binding sequences was identified (Horvath et al., 1995).

In the embodiment of the present invention where Type I interferon (see Example presented hereinbelow) and/or Type II interferon is the extracellular signal, a preferred combination of transcriptional control elements is an interferon responsive chimeric promoter in which an ISRE and/or GAS controls a SV40 minimal promoter operatively linked to a nucleotide sequence encoding a reporter gene product.

The reporter gene product, whose level is a measure of the presence and/or the level of a molecule that activates the signal transduction activity of a cell surface protein, may be RNA or protein, as long as it is readily detectable. For instance, firefly luciferase, enhanced green fluorescent protein (EGFP) and jellyfish aequorin are most preferred embodiments of reporter gene products used according to the present invention. In the case of the enzyme firefly luciferase (deWet et al., 1987) and jellyfish aequorin (Rider et al., 2003), the result of its enzymatic activity, light, is detected and measured using a luminometer, whereas in the case of EGFP, a fluorescence activated cell sorter or analyzer (FACS) can be used at an appropriate wavelength to detect and quantify the amount of EGFP expressed in a cell. The distribution curve of the amount of luciferase, aequorin or EGFP expressed in a sample of cells will be determined by the amount of ligand (within a given range) to which the cell is exposed. Non-limiting examples of other suitable reporter gene products include dsRED, chloramphenicol acetyl transferase (CAT) (Alton et al., 1979) other enzyme detection systems, such as β-galactosidase, bacterial luciferase (Engebrecht et al., 1984 and Baldwin et al. 1984), alkaline phosphatase (Toh et al. 1989 and Hall et al. 1983), and bacterial or humanized β-lactamase (Zlokarnik et al., 1998).

In order to provide the cell of the present invention, which is a one time use cell that cannot be propagated for further use, the cell transformed with a reporter gene construct is treated in such a way that it will maintain the signal transduction activity of the cell surface protein for at least about 1 hour but no more than about 30 days at a temperature above freezing before losing the signal transduction activity. Thus, according to one aspect of the present invention, which is a method for preparing a cell transformed with a reporter gene construct that loses signal transduction activity within about 30 days, a cell is transformed with a reporter gene construct containing a nucleotide sequence encoding a reporter gene product operatively linked to one or more transcriptional control elements that is regulated by the signal transduction activity of a cell surface protein in response to an extracellular signal. The transformed cell is then treated so that it will maintain the signal transduction activity of the cell surface protein for at least 1 hour but no more than about 30 days at a temperature above freezing before losing this activity.

One preferred embodiment of the present invention is where the transformed cell is treated by irradiating with γ-radiation at an intensity and for a sufficient time such the irradiated cell maintains the signal transduction activity of the cell surface protein for a period of at least about 7 days but no more than 30 days at a temperature above freezing following irradiation, after which period of time the irradiated cell immediately undergoes cellular death (i.e., apoptosis).

It is known that γ-irradiation at a high dose causes a cell to lose its signal transduction activity. Irradiation at a somewhat lower dose causes a cell to cease replication and undergo cellular death. The present inventors have now discovered that it is possible to determine a dose which inhibits replication but still allows a cell to maintains its signal transduction activity for a period of time before undergoing cell death. For example, γ-irradiation at about 9 Grays allows a cell to retain signal transduction activity for 14 days, after which the cells undergo cell death. However, during those 14 days, the signal transduction activity in response to, for example, Type I interferon that is being assayed functions as well as in a non-irradiated control. This is shown in the experiments using a luciferase gene reporter assay for Type I interferon that are presented in the Example hereinbelow. Thus, by irradiating a cell with γ radiation, the present invention provides a treated cell with a 14-day shelf life, but which becomes inactive (undergoes cellular death) after a period of about 14 days so that it cannot be maintained and reproduced by an end user.

According to the irradiation embodiment of the present invention, the dose (intensity and duration) of γ radiation to which the transformed cell is treated is preferably about 6 to 12 Grays (Gy). As the experiments in the Example presented hereinbelow demonstrate, the temperature above freezing, at which the cell is kept or stored, affects the shelf-life of the cell. Preferably, this temperature is room temperature, which advantageously maintains maximum interferon sensitivity while providing for ease of storage and shipping of the commercial one time use cell of the present invention.

A second preferred embodiment of the present invention is where the transformed cell is treated with an anti-mitotic and pro-apoptotic agent such as vinblastine, 5-fluorouracil (5-Fu), or cisplatin in a sufficient amount and for a sufficient time such that the treated cell maintains the signal transduction activity of the cell surface protein for a period of at least about 1 hour but no more than about 30 days at a temperature above freezing following treatment with the agent, after which period of time the treated cell immediately undergoes cellular death. An anti-mitotic and pro-apoptotic agent will affect a treated cell when it begins to replicate, thereby inducing apoptosis and killing the cell. Thus, cells which have been treated with an anti-mitotic and pro-apoptotic agent, such as the human promonocytic cells transformed with a luciferase reporter gene construct exemplified in the Example hereinbelow, will have a shelf life of about 24 hours during which the signal transduction assay can be conducted and after which period of time the cells will die. It will be appreciated that cell having only a 24 hour shelf life is not desirable from a commercial standpoint. In order to extend the shelf life, the treated cells may be immediately frozen, in which state they will have a much longer shelf life, depending upon the manner of freezing and thawing. Once thawed, however, they must be used within 24 hours, after which they will undergo cellular death (i.e., apoptosis).

It should be understood that conventional wisdom is that cryopreservation of cells requires a special freezing and thawing process (and equipment) in which the cells are frozen at a rate of 1° C. per minute until it reaches −80° C. or liquid nitrogen temperatures of about −200° C., where it may be stored indefinitely, and after which it must be thawed very rapidly. Often, dimethyl sulfoxide (DMSO) or another cryopreservative is also used in order to help protect the cells. If the cells are treated with an anti-mitotic and pro-apoptotic agent, they can be frozen with this cumbersome cryopreservation technique for an indefinite period of time and then be used for a purpose, such as a gene reporter assay for signal transduction activity, for 24 hours after being thawed. However, this is considered a less commercially viable technique as it would greatly increase the manufacturing/processing cost.

As most laboratories do not have storage facilities at −200° C. or even −80° C., it would be useful to allow freezing of the cells to occur at −20° C. However, it is known that cell viability is poor when cells are frozen at −20° C. and then thawed. In the course of the experimentation leading to the present invention, it was unexpectedly discovered by the present inventors that DMSO will protect the cells even when frozen at −20° C. without any special freezing or thawing techniques or equipment. While glycerol, a known cryopreservative compound, will protect cells at −20° C., there is the possibility that it may prevent protein ligands from interacting with surface receptors at the high percentage (50%) of glycerol conventionally used for cryopresevation. However, a low percentage of glycerol (much less than the 50% conventionally used) can be used. DMSO does not have this disadvantage. It is a discovery of the present invention that DMSO will protect cells frozen at −20° C. without any special freezing or thawing techniques or equipment being required and without adversely affecting their sensitivity to IFN as demonstrated in the Example hereinbelow (see FIG. 11). Thus, it is another surprising and inventive aspect of the present invention that after treating with an anti-mitotic and pre-apoptotic agent, a cell may achieve a long shelf life even at standard freezer temperatures of −20° C. if further treated with DMSO and that once thawed such a cell will remain active, i.e., for signal transduction assays, for approximately 24 hours until it undergoes apoptosis as a result of being treated with an anti-mitotic and pro-apoptotic agent. Any anti-mitotic and pro-apoptotic agent which kills cells during the process of replication by inducing apoptosis, such as vinbastine, 5-FU and cisplatin, can be used for this purpose as it would be expected that the cells will remain biologically active during a quiescent period and until such time the treated cells start to die.

Thus, according to a second preferred embodiment of the present invention, the treated transformed cell is frozen at a temperature and under conditions such that it will resume signal transduction after thawing. While the cell is preferably frozen at a temperature between −20° C. and −200° C., more preferably at −80° C., and subsequently stored at −20° C., a commonly available freezer temperature in almost all laboratories, it is intended that other suitable temperatures for cryopreservation of cells, such as the liquid nitrogen temperature of about −200° C., be encompassed by the present invention. It is further preferred that the treated transformed cell be resuspended in a solution containing a cryopreservative before freezing the cell. Dimethyl sulfoxide (DMSO) is the preferred cryopreservative although other suitable cryopreservatives which have a high bonding affinity to water, such as ethylene glycol, polyethylene glycol, propylene glycol, glycerol, butane diol, propanediol, and formamide, may be used so long as they do not interfere with the use of the cell after thawing. When DMSO is used alone as the cryopreservative, the solution containing DMSO preferably contains about 10% DMSO. More preferably, 2.5% DMSO is used in combination with 10% glycerol as the cryopreservative.

Another aspect of the present invention is directed to an assay kit for determining the level in a sample of a molecule that activates the signal transduction activity of a cell surface protein. This assay kit includes a plurality of the cell of the present invention (as a reagent) and a testing device having a plurality of wells. Preferably, the testing device is a multi-well microtiter plate, but can also be any type of receptacle, such as petri dishes or plates, with a plurality of wells in which an assay can be conducted to determine the level of a molecule in a sample. It is preferred that the cells as a component or reagent of the assay kit be disposed in the wells of the testing device, although it will be appreciated that such cells can instead be dispensed in the wells of the testing device by the end user just prior to conducting the assay. The kit may further include a set of instructions for using the kit to conduct the intended assay for determining the level of a molecule that activates the signal transduction activity in a sample.

The present invention further provides an assay method for determining the presence and/or the level in a sample, by reference to a standard included in the assay, of a molecule that activates the signal transduction activity of a cell surface protein, preferably a cell surface receptor. This assay method uses the cell of the present invention and can include the method of preparing such a cell according to the present invention as its initial step or steps. If the prepared cell is frozen according to a preferred embodiment of the present invention, then the cell must be thawed before proceeding to incubate it with a sample in which the presence and/or the level of a molecule that activates the signal transduction activity of a cell surface protein is sought to be determined. In one preferred embodiment where the cell is irradiated with γ radiation, the cell is preferably maintained and stored at room temperature until use. As the cell is not frozen, a thawing step is unnecessary. After incubation, the level of expression of a reporter gene product, encoded in the reporter gene construct carried by the prepared cell, is determined in the sample. This level of expression as determined by the method according to the present invention is used to then qualitatively determine the presence and/or quantitatively determine the level in a sample of the molecule that activates the signal transduction activity of a cell surface protein.

Figure 1:
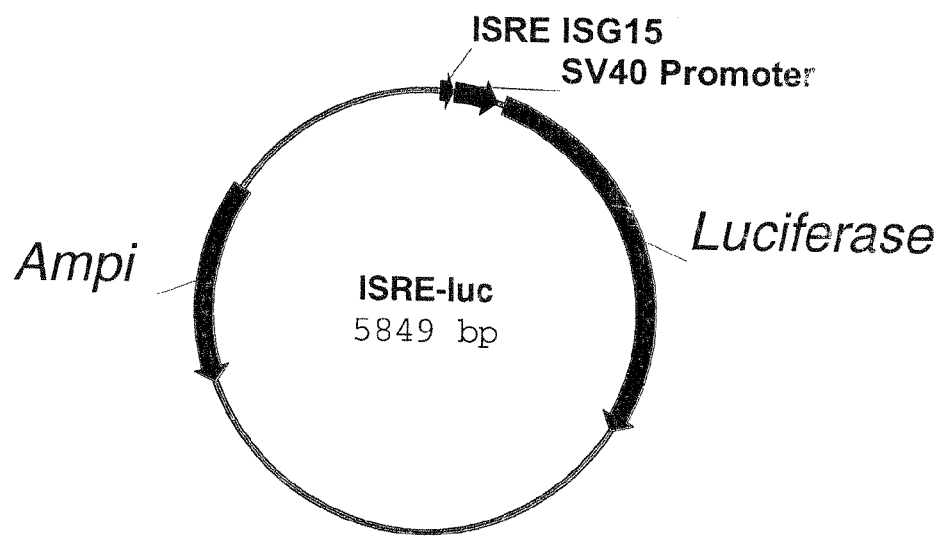
FIG. 1 shows a schematic representation of a luciferase reporter gene construct where luciferase expression is under the control of a chimeric promoter containing an interferon sensitive response element (ISRE) from the ISG15 gene and a minimal SV40 promoter.
Figure 2:
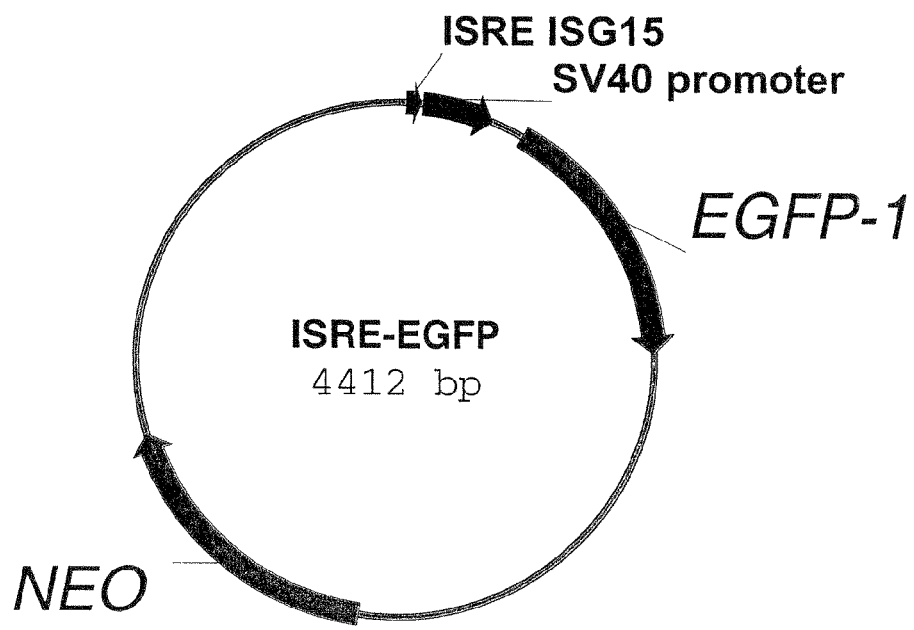
FIG. 2 shows a schematic representation of an enhanced green fluorescent protein (EGFP-1) reporter gene construct where EGFP-1 expression is under the control of a chimeric promoter containing an ISRE from the ISG15 gene and a minimal SV40 promoter.

A gene reporter assay for Type I interferon is a most preferred embodiment of the present invention. The reporter gene product is preferably firefly luciferase, jellyfish aequorin, or or enhanced green fluorescent protein (EGFP) and is preferably under the control of an interferon sensitive chimeric promoter containing the ISRE from ISG15 and a minimal SV40 promoter. Examples of such reporter gene constructs are presented in FIGS. 1 and 2. FIG. 1 is a schematic representation of a luciferase gene reporter construct in an ISRE-luc vector (SEQ ID NO:1), where the ISRE from ISG15 (SEQ ID NO:5) is positioned at nucleotides 38-97 of SEQ ID NO:1, the SV40 minimal promoter is positioned at nucleotides 103-288 of SEQ ID NO:1, and the coding sequence of the luciferase reporter gene having the amino acid sequence of SEQ ID NO:2 is positioned at nucleotides 328-1980 of SEQ ID NO:1. Similarly, FIG. 2 is a schematic representation of a EGFP gene reporter construct in an ISRE-EGFP vector (SEQ ID NO:3), where the ISRE from ISG15 is positioned at nucleotides 30-89 of SEQ ID NO:3, the SV40 minimal promoter is positioned at nucleotides 95-290 of SEQ ID NO:3, and the coding sequence of the EGFP reporter gene having the amino acid sequence of SEQ ID NO:4 is positioned at nucleotides 358-1077 of SEQ ID NO:3.

As for the cell used in the preferred gene reporter assay for Type I interferon embodiment of the present invention, the cell is preferably a mammalian or avian cell, more preferably a human cell, and most preferably a human promonocytic cell. A preferred human promonocytic cell carrying the ISRE-luc vector containing the luciferase gene reporter construct is a PIL5 cell. The cell is treated to make a commercial cell line that has the commercially desirable properties of a sufficient shelf life for the purpose of the assay and of being a one time use cell that cannot be propagated for possible further use. Preferably, the cell is treated either 1) by irradiating with 6 to 12 Gy of γ radiation, more preferably about 9 Gy, and storage at room temperature for up to 14 days after irradiation or 2) by exposure to an anti-mitotic and pro-apoptotic agent, such as vinblastine, cisplatin, or 5-fluorouracil, most preferably vinblastine, for 10 minutes at 37° C. prior to resuspending in a solution containing 40% fetal bovine serum (FBS) and 2.5% DMSO+10% glycerol and freezing at −80° C.

In order to optimize the method of obtaining a cell with an indefinite shelf life during frozen storage, but which will die approximately 24 hours after being thawed (once thawed, however, the product has excellent sensitivity, and precision as well as selectivity), the parameters which can be varied in the course of such optimization include:

1) Concentration of FBS. Besides FBS, most any serum could be used as it acts as a toxic sink to protect the cells from toxins, such as while being thawed or while being treated with an anti-mitotic and pro-apoptotic agent. The concentration of FBS can cause the results to vary.

2) Time is a variable. The amount of time of exposure to vinblastine before the cells are centrifuged out and washed to remove vinblastine.

3) The formulation of the vinblastine makes a difference. Presently, soluble vinblastine in a proprietary prebuffered formulation sold by Eli Lilly under the name Velbe in France is preferably used. A different formulation may require slightly different combination of parameters.

4) The concentration of vinblastine.

5) Cell concentration during the vinblastine treatment.

6) The amount of cryopreservative or combination of cryopreservatives.

All of these parameters can be varied empirically and the results after freezing tested for sensitivity and precision, assuming that the cells stay alive for approximately 24 hours after being thawed. This can be readily determined by one of ordinary skill in the art without undue experimentation, particularly in view of the guidance provided in the experiments shown in FIGS. 11-24 for PIL5 cells, in order to arrive at a product having substantially the same sensitivity as the untreated live cells for a period of at least one hour, preferably 8 hours, following thawing but having a viability of no more than 30 days.

A most preferred embodiment of the present invention is exemplified below in the form of a procedure for conducting a luciferase gene reporter assay for Type I interferon using PIL5 cells treated with the anti-mitotic and pro-apoptotic agent 1 μg/ml vinblastine for 10 minutes at 37° C. prior to frozen storage at −20° C. and thawing at a later time for purposes of conducting the assay.

Protocol for Luciferase Gene Reporter Assay for Type I Interferon Using Treated PIL5 Cells Preparation of Microtiter Assay Plates
1. PIL5 cells at a concentration of about $2 \times 10^5$ to $7 \times 10^5$ cells/ml in RMPI 1640 medium with 10% fetal bovine serum (FBS) are treated with a fresh solution of 1 μg/ml vinblastine (commercially available from Eli Lilly under the pre-buffered formulation VELBE), diluted from 1 mg/ml in $H_2O$, for 10 minutes at 37° C. in an atmosphere of 5% $CO_2$ in air. A $CO_2$ incubator can be used for convenience.
2. The PIL5 cells are centrifuged at 800×g for 10 minutes at 4° C., and washed once with the same volume of RPMI 1640 medium with 10% FBS to remove the vinblastine.
3. The PIL5 cells are re-suspended at a concentration of $2 \times 10^7$ cells/ml in RMPI 1640 medium with 40% fetal bovine serum (FBS) and 2.5% dimethylsulfoxide+10% glycerol.
4. The cell suspension is dispensed into the wells of a flat-bottom micro-plate to give 300,000 cells per well (equivalent to 25 μl of cell suspension per well).
5. The micro-plate is frozen at −80° C. in an aluminum bag sealed under vacuum with the cover uppermost.
6. The micro-plates can be subsequently stored at −20° C. until use.

Preparation of Cryopreservation Ampoules/Vials
1. PIL5 cells at a concentration of about $2 \times 10^5$ to $7 \times 10^5$ cells/ml in RMPI 1640 medium with 10% fetal bovine serum (FBS) are treated with a fresh solution of 1 μg/ml vinblastine (commercially available from Eli Lilly under the prebuffered formulation VELBE), diluted from 1 mg/ml in $H_2O$ for 10 minutes at 37° C. in an atmosphere of 5% $CO_2$ in air. A $CO_2$ incubator can be used for convenience.
2. The PIL5 cells are centrifuged at 80×g for 10 minutes at 4° C., and washed once with the same volume of RPMI 1640 medium with 10% FBS to remove the vinblastine.
3. The PIL5 cells are re-suspended at a concentration of $2 \times 10^7$ cells/ml in RMPI 1640 medium with 40% fetal bovine serum (FBS) and 2.5% dimethylsulfoxide+10% glycerol.
4. The cell suspension (1 ml) is dispensed into a cryopreservation vial and frozen at −80%.
5. The cryopreservation vial can be subsequently stored at −20° C. until use.

The assay procedure described below is directed to using the microtiter assay plates prepared above. However, in case the end user elects to obtain the treated PIL5 cells in cryopreservation vials instead of in microtiter plates as predispensed aliquots, the end user may dispense 75 μl of the treated PIL5 cells into each well of a microtiter plate of his/her choice following dilution of the cells 1:6 in RPMI 1640 medium with 10% FBS or into some other receptacles, i.e., Eppendorf microfuge tubes, and conduct the assay in a similar fashion as described below.

Assay Procedure
Preparation of Standard Curve
1. Remove protective cover from the sample preparation micro-plate (Plate A).
2. Add 100 μl of the diluent (RPMI 1640 medium without serum) to wells A1 through A6 and B1 through B6 of the sample preparation plate (Plate A).
3. Add 100 μl of the interferon (IFN) reference preparation to wells A1 and B1 of Plate A containing 100 μl of diluent.
4. Carry out serial two-fold dilutions of the IFN reference preparation in Plate A from wells A1 and B1 through wells A6 and B6 using a multi-channel micro-pipette.

Sample preparation
1. Add 100 μl of the diluent to the wells of the sample preparation plate (Plate A) where required.
2. Dilute samples to be tested if the estimated IFN titer of the samples is greater than 100 IU/ml.
3. Dilute samples appropriately in the sample preparation micro-plate (Plate A)

Assay Procedure
1. Rapidly thaw the 96-well PIL5 assay micro-plate (Plate B) on a flat surface with the cover uppermost. A waterbath set at 37° C. can be used for convenience.
2. Dry protective cover with a paper hand towel, taking care to maintain the label uppermost.
3. Carefully remove protective cover from the PIL5 assay micro-plate (Plate B) while maintaining the cover uppermost.
4. Add 75 μl of each of the serial two-fold dilutions of the reference preparation to wells A1 and B1 through wells A6 and B6 of the PIL5 assay micro-plate (Plate B) using a multi-channel micro-pipette.
5. Add 75 μl of each undiluted or appropriately diluted sample to the PIL assay micro-plate (Plate A).

6. Incubate the PIL5 assay micro-plate (Plate B) overnight at 37° C. in an atmosphere of 5% $CO_2$ in air. A $CO_2$ incubator can be used for convenience.
7. Add 100 μl of LUCLIT PLUS (Packard Biosciences, Inc., now part of PerkinElmer Life Sciences, Boston, Mass., catalog #6016961) to each well of the PIL5 assay micro-plate (Plate B) using a multi-channel micro-pipette.
8. Determine the luminescence of the samples using a micro-plate luminometer (LUMICOUNT, Packard).

Calculation of International Units

1. Plot standard curve from the mean of the luminescence readings for each dilution of the IFN reference preparation calibrated against the NIH international reference standard for HuIFN-α (G-023-901-527) using Microsoft EXCEL.
2. The equation describing the stand curve is obtained using the EXCEL function "interpolation of the curve" using the option "exponentionel curve". This equation is then used to calculate the IFN titer of each sample expressed in international units (IU).

While the present invention is directed to commercializing any cell engineered for signal transduction assays, such as those described in U.S. Pat. Nos. 5,436,128 and 5,401,629, the entire contents of which are incorporated herein by reference, there are specific and important utilities for the most preferred embodiments of a gene reporter assay for Type I interferon and the cell used in such an assay. For example, the cell in the interferon gene reporter assay can serve as a surrogate marker for viral infection. It is known that circulating interferon is indicative of a virus infection but circulating interferon does not usually appear in a person who has a bacterial infection. Thus, if a person is suspected of having an infection and one wants to determine whether the infection is viral or bacterial so that treatment can be efficacious and specifically targeted to either a viral or bacterial infection, this interferon gene reporter assay would be extremely useful. In HIV patients, it is known that the circulating interferon level becomes detectable towards the end of the asymptomatic period. Thus, interferon monitoring indicative of disease progression is another utility.

The cell in the interferon gene reporter assay can also be used as a surrogate marker for detecting viral infections caused by bioterrorism in a susceptible population. If random blood samples are taken in a susceptible population, this simple gene reporter assay allows a relatively fast and inexpensive determination of ubiquitous viral infection which would be an indication of a possible bioterrorism attack.

Furthermore, rat cell lines, bovine cell lines, avian cell lines, etc., can be created which have the reporter gene under the control of an ISRE in order to determine if animals are infected with a virus, such as to detect bubonic plague in rats, West Nile virus in birds (i.e., crows), hoof and mouth disease in cattle, etc. The presence of West Nile virus in humans can be readily distinguished from most other viral infections because it is one of only a few viral infections that cause a titer of Type I interferons to quickly reach into the tens or hundreds of thousands of units in humans.

Another utility is to monitor interferon therapy in patients to see how much interferon is actually entering the bloodstream (i.e., from sub-lingual administration) and to determine patient compliance if doses of interferon are self administered.

As a further utility, the cell and interferon reporter assay can be used to detect autoimmune diseases, such as systemic lupus erythematosus (SLE), Type I diabetes, multiple sclerosis, psoriasis, or rheumatoid arthritis (RA), which are characterized by the presence of interferon in the peripheral circulation or in other body fluids, such as synovial fluids in the case of RA, or to determine the stage of an autoimmune disease. Often these diseases have stages of exacerbation and remission which manifest within the diseased tissue with an increase in circulating interferon immediately prior to an exacerbation phase. Thus, this assay can be used to detect when a patient may be about to enter an exacerbation stage and may offer an opportunity for treatment to prevent or ameliorate the exacerbation stage.

Figure 3:
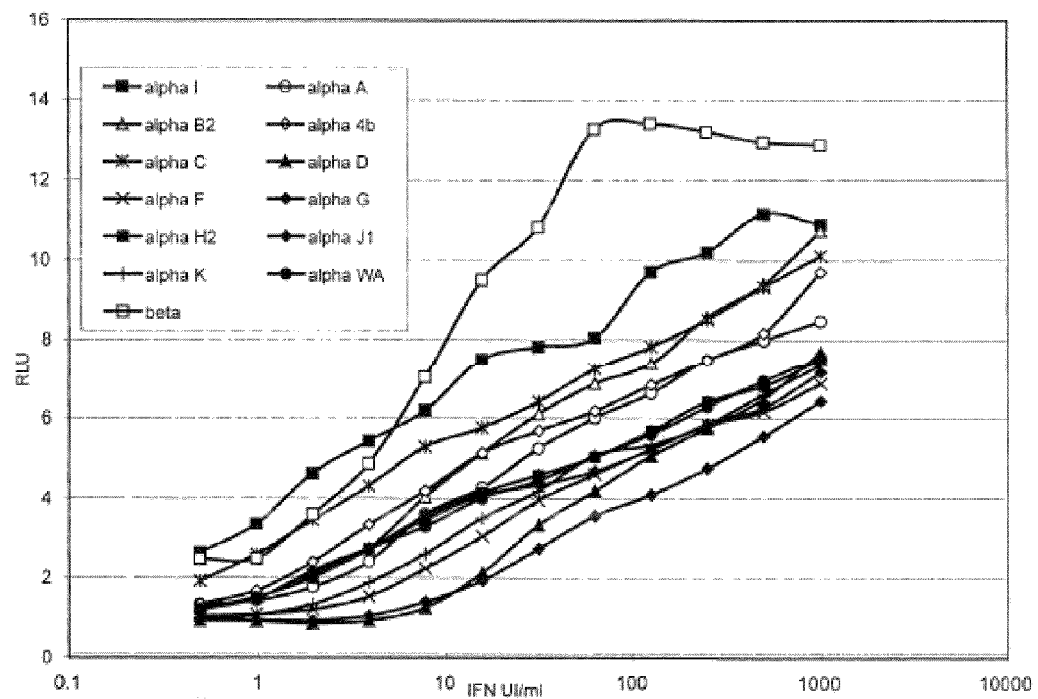
FIG. 3 shows the standard curves of luciferase activity in PIL5 cells in the presence of different amounts of each of the various isotypes of human Type I interferon.

The present interferon reporter assay recognizes any Type I interferon which binds to a Type I interferon receptor. It is possible, however, to determine which isotype(s) of interferon is being detected by using a parallel monoclonal antibody treatment. Thus, a monoclonal antibody for a specific isotype of interferon will prevent that isotype of interferon from causing signal transduction. If the signal disappears in the presence of antibody, then it is known that the particular interferon being detected is the isotype to which the antibody is specific. The standard activity curve for different isotypes of interferon differ in any given reporter cell line such as for the PIL5 cell line shown in FIG. 3. Such standard activity curves can be generated for each type of interferon in a given reporter cell line. Using such standard curves, one can accurately quantitate the level of interferon present in a sample once it is known what isotype of interferon is being detected.

Finally, the present invention in general provides a method for commercializing cells having a desired biological activity. This commercial method involves treating cells such that the cells will maintain the desired biological activity for no more than 30 days at a temperature above freezing, and then freezing the treated cells at a temperature and under conditions such that they will resume the required biological activity after thawing. The frozen treated cells, which are available for a limited time but cannot be propagated and maintained indefinitely for multiple uses, are subsequently sold or distributed. The cells are preferably treated with an anti-mitotic and pro-apoptotic agent in a sufficient amount and for a sufficient time such that the treated cells will maintain the desired biological activity for at least 8 hours, but no more than about 30 days at a temperature above freezing. It is preferred that the temperature at which the cells are frozen be about −80° C. and that the cells are resuspended in RPMI 1640 medium with 40% FBS containing cryopreservatives, preferably 2.5% DMSO+10% glycerol, prior to freezing.

Having now generally described the invention, the same will be more readily understood through reference to the following example which is provided by way of illustration and is not intended to be limiting of the present invention.

EXAMPLE

The present inventors have overcome the disadvantages of current methods of quantifying interferons by developing a highly sensitive and reproducible method for quantifying IFN activity based on the establishment of a human cell line transfected with the luciferase reporter gene placed under the control of an IFN responsive chimeric promoter. This method of the present invention allows IFN activity to be determined in a few hours rather than in the 3 to 4 days required for a bioassay. Briefly, the interferon stimulatory response element (ISRE) from the ISG15 gene controlling a SV40 minimal promoter was cloned upstream of the luciferase reporter gene in a 5849 bp ISRE-luc vector (FIG. 1; SEQ ID NO:1). Alternatively, the ISRE from the ISG15 gene controlling a SV40 minimal promoter is cloned upstream of an enhanced green florescent protein (EGFP-1) reporter gene in a 4412 bp ISRE- EGFP vector (FIG. 2; SEQ ID NO:3). Human promonocytic U937 cells were transfected with the IFN regulated gene reporter construct and stable transfectants were isolated and cloned. A human cell line PIL5 carrying the luciferase reporter gene under the control of an IFN responsive chimeric promoter was thus established and provides the basis of an assay which allows IFN activity to be determined more rapidly and with greater precision than the standard antiviral bioassay (Lallemand et al., 1996). Table 1 presents the advantages of the luciferase gene reporter assay for interferon using PIL5 cells over the standard antiviral bioassay and Table 2 presents a comparison between the luciferase gene reporter assay for interferon using PIL5 cells and the standard antiviral bioassay on sensitivity to interferon produced as a result of infection by various viruses.

TABLE 1

|  | GENE REPORTER ASSAY | BIOASSAY |
| --- | --- | --- |
| Sensitivity | 0.1 IU | 1 to 5 IU |
| Response time | 4-8 hrs | 3 to 4 days |
| Use | General | Restricted |
| Cost | Reagent and labour costs low | High reagent costs |
|  | >90% gross margin | Labour intensive |

TABLE 2

| Gene Reporter Assay IU/ml | Bioassay IU/ml | Etiology |
| --- | --- | --- |
| >50 | 25 | Adenovirus |
| 17 | 6 | IFN treatment |
| >50 | 37 | Influenza B |
| >50 | 25 | Para Influenza I |
| 30 | 9 | HIV |
| 45 | 12 | HIV |
| >50 | 37 | Rotavirus |
| 2 | Undetected | HCV |
| 4 | Undetected | HCV |

The gene reporter assay using PIL5 cells is highly sensitive (less than 1.0 IU/ml of IFNα or IFNβ can be detected routinely), reproducible (standard error +/−10%), and can detect IFN activity over a wide range of concentrations (0.1 to 100 IU/ml). The method is also highly specific and can for example even detect low levels of Type I IFNs (IFNα or IFNβ) in the presence of high levels of IFNγ which is not possible using a conventional antiviral bioassay. The method is ideally suited for the determination of IFN activity in biological fluids such as human serum, cerebrospinal fluid, or urine as the method is less subject to non-specific interference at low dilutions than the conventional anti-viral bioassay. Human serum and other biological fluids often contain non-specific inhibitors of virus-replication unrelated to IFN which can affect virus replication at low dilutions giving rise to false positives.

The PIL5 gene-reporter IFN assay recognizes any Type I interferon which binds to a Type I interferon receptor. It also provides a means of distinguishing between one IFNα sub-type and another due to the ability to detect differences in the dose response (standard) curves characteristic of individual IFNα sub-types. This is of considerable value in distinguishing between different virus infections. Paramyxo viruses such as Sendai induce mainly IFNα1, IFNα2, and IFNβ, while Lentiviruses such as HIV-1 induces mainly IFNα5 (Lallemand et al., 1996). Standard curves of luciferase activity in PIL5 cells in the presence of different amounts of each of the various isotypes of interferon is presented in FIG. 3.

Thus, a method has been developed for the determination of IFN levels in biological fluids which has been used experimentally to analyze numerous clinical samples from virus infected individuals. The method is rapid, inexpensive, robust, does not require specialized personnel or equipment, and is readily automated. The PIL5 gene-reporter assay is based, however, on the use of live cells which limits commercialization in its present form, due to a severely limited shelf life and the ability of a customer to retain and cultivate the PIL5 cell line thereby obviating the necessity to purchase further kits. The experiments presented below were conducted to develop a modified form of the PIL5 gene reporter assay amenable to commercialization in a kit format, where the PIL5 cells are treated so as to have a sufficiently long shelf life as part of a commercial assay, and whereupon at the end of its useful shelf life or at the end of its use in a PIL5 gene reporter assay, the treated PIL5 cells undergo cellular death such as by apoptosis. The experimental approach adopted as described below is based on the use of fractionated doses of γ irradiation or on the use of anti-mitotic and pro-apoptotic agents to prevent cell multiplication and to induce delayed cellular death (i.e., apoptosis) while retaining a functional IFN signal transduction pathway.

Effect of γ Irradiation on IFN Sensitivity

Figure 4:
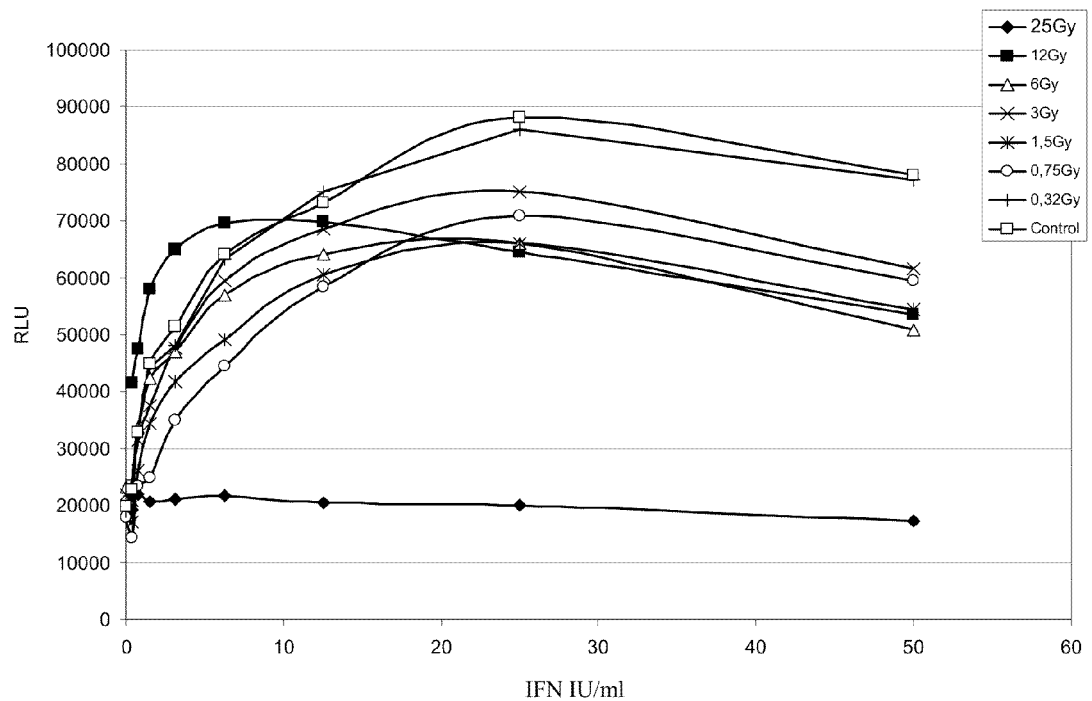
FIG. 4 is a graph showing luciferase activity in PIL5 cells four days after different doses of γ radiation and incubation at 37° C.
Figure 5:
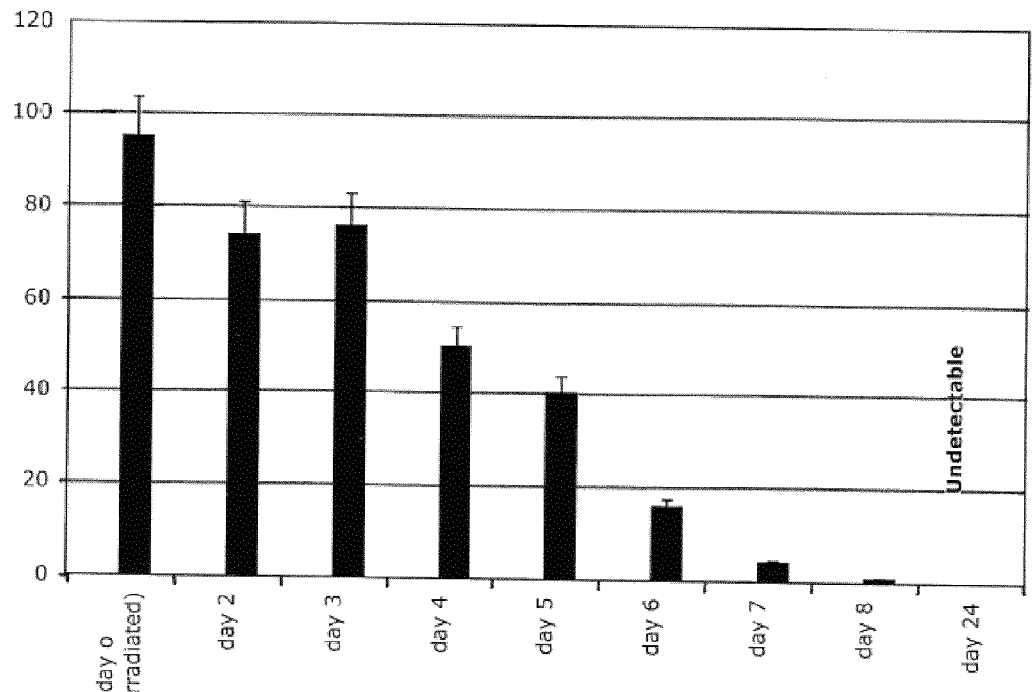
FIG. 5 is a graph showing the percentage of viable PIL5 cells at various times after 6 Grays (Gy) of γ radiation and incubation at 37° C.

PIL5 cells were subjected to increasing doses of γ irradiation (0.32 to 25 Gy) and then tested at various times thereafter for their ability to detect increasing doses of Type I interferons. The results of preliminary experiments indicated that PIL5 cells retain full IFN sensitivity when incubated at 37° C. for up to 4 days after doses of γ irradiation between 0.32 and 12 Gy (FIG. 4), and that apoptosis is induced in 100% of the cell population exposed to doses of γ irradiation of 6 to 25 Gy (Table 3). Thus, these results validated the experimental approach adopted and suggested that the potential shelf life of the PIL5 gene reporter assay could be extended significantly beyond 4 days by exposing cells to fractionated doses of γ irradiation within the range of 6 to 12 Gy while inducing 100% (or nearly 100% for 6 Gy) apoptosis of the cell population (FIG. 5 and Table 3).

TABLE 3

Percentage of Cells Viable after Irradiation

| Time After Irradiation | 25 Gy | 12 Gy | 6 Gy | 3 Gy | 1.5 Gy | 0.75 Gy | 0.32 Gy | Control |
|---|---|---|---|---|---|---|---|---|
| Day 1 | 100 | 100 | 100 | 100 | 100 | 100 | 100 | 100 |
| Day 2 | 60 | 100 | 100 | 100 | 100 | 100 | 100 | 100 |
| Day 3 | 40 | 80 | 100 | 100 | 100 | 100 | 100 | 100 |
| Day 4 | 30 | 50 | 80 | 100 | 100 | 100 | 100 | 100 |
| Day 8 | 0 | 0 | 0 | 50 | 50 | 100 | 100 | 100 |
| Day 21 | 0 | 0 | 100 | 100 | 100 | 100 | 100 | 100 |

Effect of Temperature on IFN Sensitivity

Figure 6:
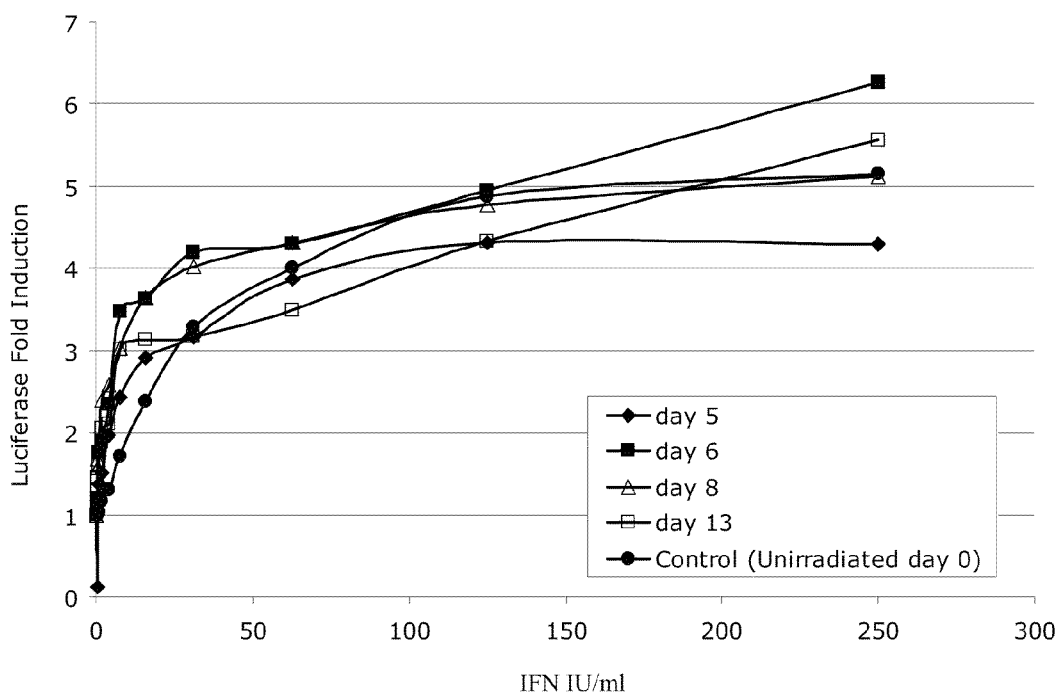
FIG. 6 is a graph showing luciferase activity in PIL5 cells at various times after 6 Gy of γ radiation and incubation at room temperature.
Figure 7:
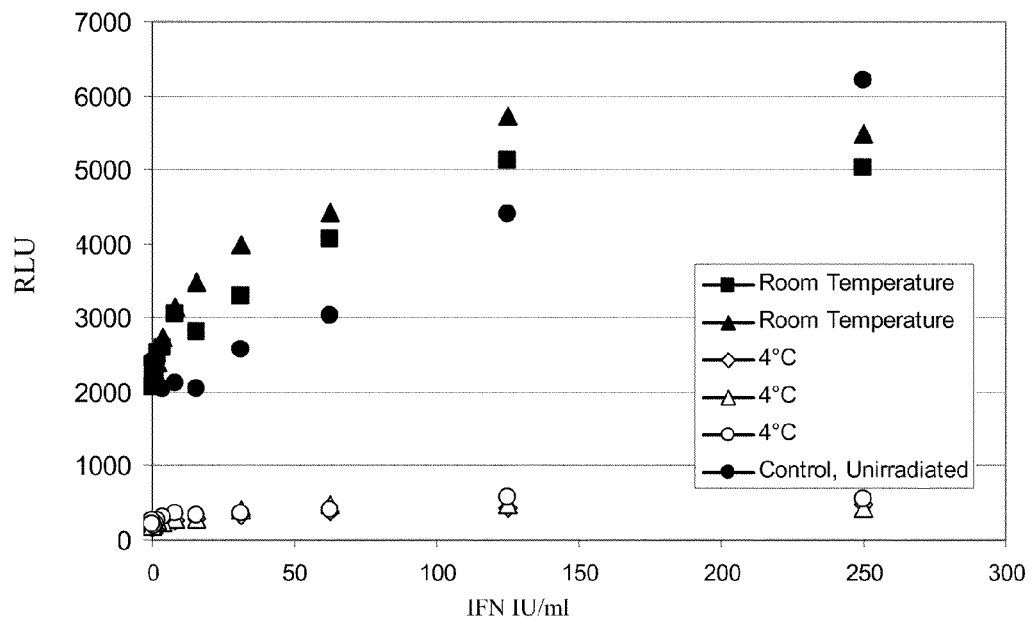
FIG. 7 is a graph showing luciferase activity in PIL5 cells eight days after 6 Gy of γ radiation and incubation at 4° C. or room temperature.

The results of a series of experiments have established that PIL5 cells can indeed be stored in RPMI 1640 medium with 10% fetal calf serum for up to 13 days at room temperature following exposure to a dose of γ irradiation of 6 Gy and still retain full IFN sensitivity (FIG. 6). That is provided that the PIL5 cells are subsequently incubated with the test samples or IFN standard at 37° C., prior to assaying luciferase activity. In contrast, it has been unexpectedly shown that incubation of PIL5 cells at 4° C. in RPMI 1640 medium with 10% fetal calf serum following exposure of the cells to a dose of γ irradiation of 6 Gy induced cell death. This resulted in a marked loss of IFN sensitivity after only 8 days incubation at 4° C. (FIG. 7).

Effect of Serum Concentration on IFN Sensitivity

Figure 8:
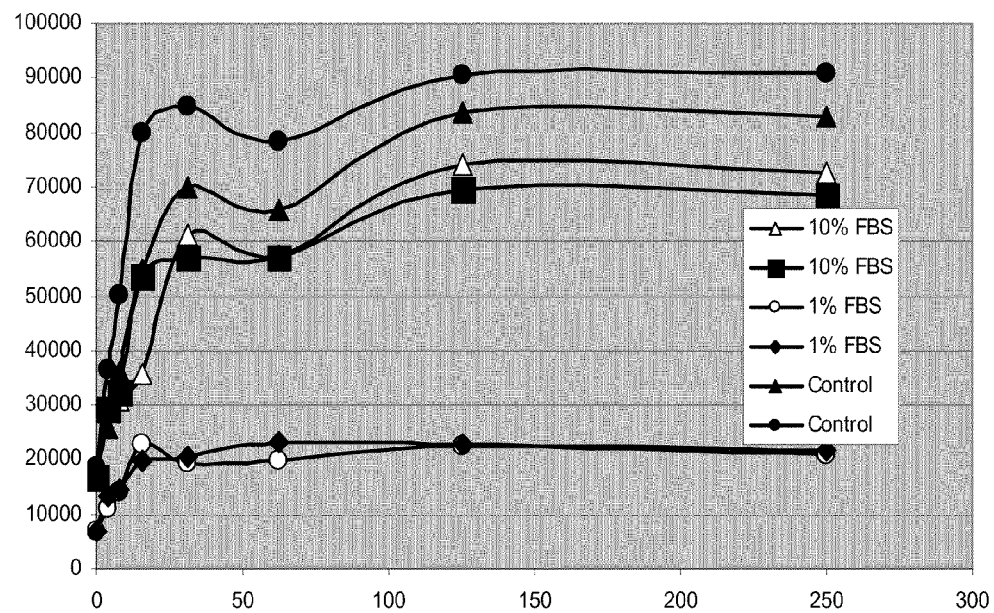
FIG. 8 is a graph showing luciferase activity in PIL5 cells five days after 6 Gy of γ radiation and incubation at 37° C. in culture medium containing 0%, 1%, or 10% fetal bovine serum (FBS).

In an additional series of experiments, the serum content of the culture medium was varied between 1 and 10% in order to modulate exposure of cells to serum growth factors, the signalling of which is known to counter the induction of apoptosis by γ irradiation. The results of these experiments showed that induction of apoptosis in PIL5 cells is more rapid when the cells are incubated in culture medium containing 1% fetal bovine serum (indicated as FBS in FIG. 8) serum than in culture medium containing 10% serum (FIG. 8). Furthermore, increasing the serum concentration from 10 to 20% did not affect significantly cell viability.

Effect of Cell Concentration on IFN Sensitivity

Figure 9:
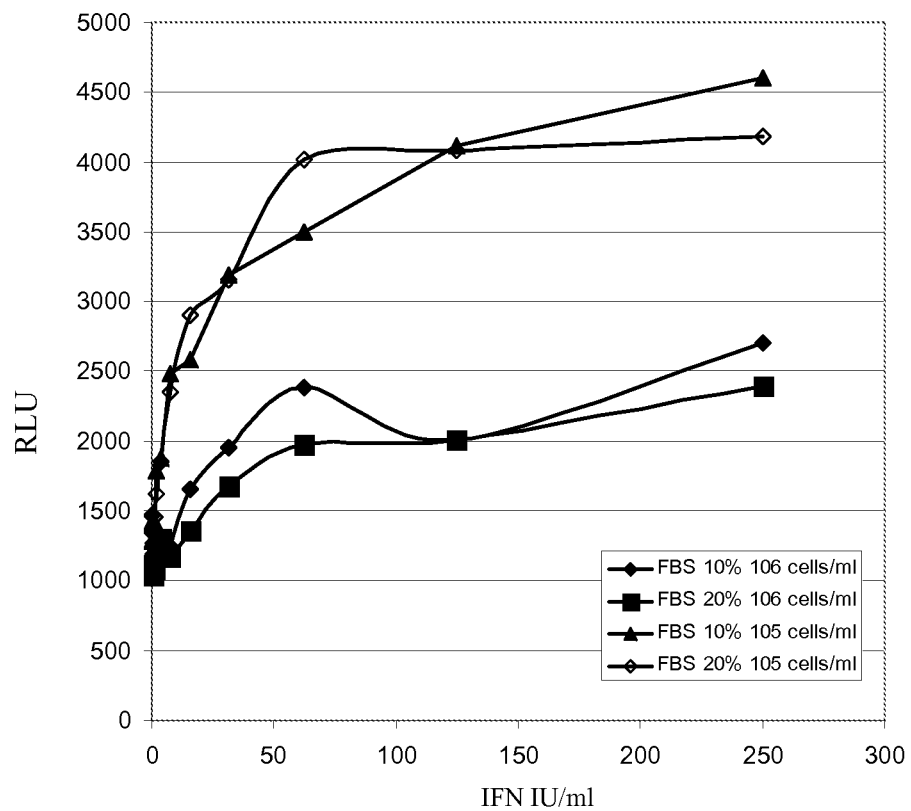
FIG. 9 is a graph showing luciferase activity in different cell concentrations of PIL5 cells thirteen days after 6 Gy of γ radiation and incubation at 37° C. in culture medium containing 10% or 20% fetal bovine serum (FBS).

It was expected that the sensitivity of the present PIL5 IFN gene reporter assay could be increased significantly simply by increasing the number of PIL5 cells used in the assay. Such a super high sensitivity (SHS) version of the PIL5 gene reporter assay would find wide application for the determination of very low levels of IFN in biological fluids such as cerebrospinal fluid. Thus, PIL5 cells were incubated at concentrations of 0.1 to $1.0 \times 10^6$ cells/ml at room temperature in culture medium containing 10% fetal bovine serum following exposure to a dose of 6 Gy of γ irradiation and then tested at various times thereafter for their ability to detect increasing doses of IFN α. The results of these experiments showed that, although interferon sensitivity was indeed increased initially, incubation of PIL5 cells at high cell density induced cellular death more rapidly than at a concentration of $0.1 \times 10^6$ cells/ml, most probably due to depletion of growth factors in the culture medium or production of toxic metabolites (FIG. 9).

Effect of the Inhibitors of Apoptosis Phenylarsine Oxide and Aurintricarboxylic Acid on IFN Sensitivity In an attempt to extend the shelf-life of the PIL5 IFN assay, PIL5 cells were subjected to 6 Gy of γ irradiation and then treated with increasing concentrations (0, 0.1, 1.0, 10, and 100 μM) of aurintricarboxylic acid or phenylarsine in order to modulate the induction of apoptosis. The cells were then tested at different times thereafter (0, 5, 10, 15, 20 days etc) for IFN sensitivity.

Figure 10:
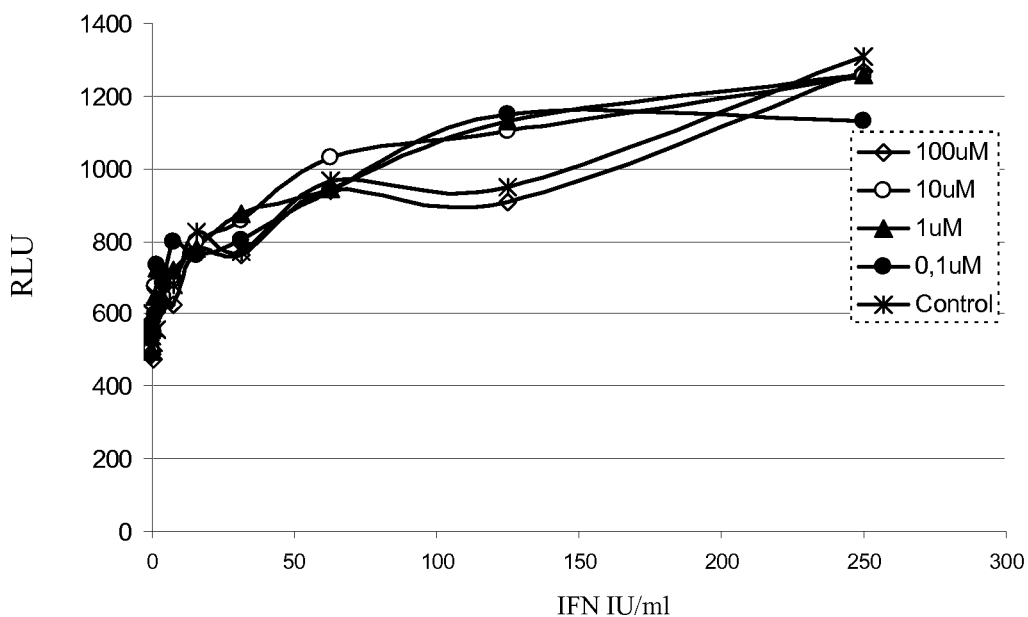
FIG. 10 is a graph showing luciferase activity in PIL5 cells fourteen days after 6 Gy of γ radiation and treatment with aurintricarboxylic acid at room temperature.

The results of these studies showed that the addition of increasing concentrations of aurintricarboxylic acid did not extend the shelf life of PIL-5 gene reporter following exposure of cells to a dose of 6 Gy of γ irradiation (FIG. 10).

Figure 11:
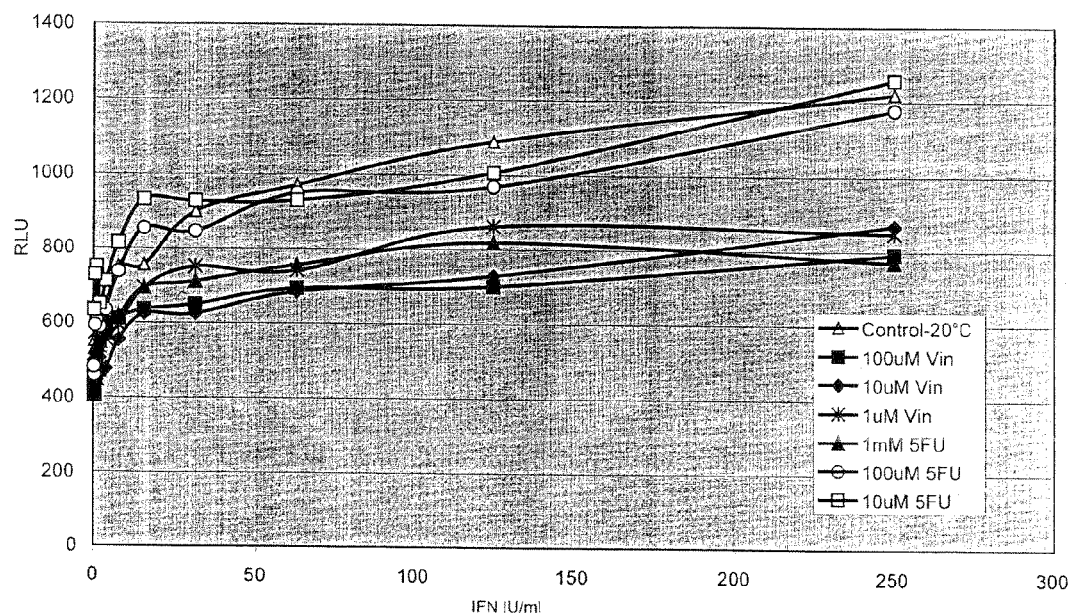
FIG. 11 is a graph showing luciferase activity in PIL5 cells 24 hours after thawing from 1 month storage at −20° C. in 10% DMSO. The PIL5 were treated for 1 hour with different concentrations of anti-mitotic and pro-apoptotic agents, vinblastine (Vin) or 5-fluorouracil (5Fu), prior to freezing and storage at −20° C.
Figure 12:
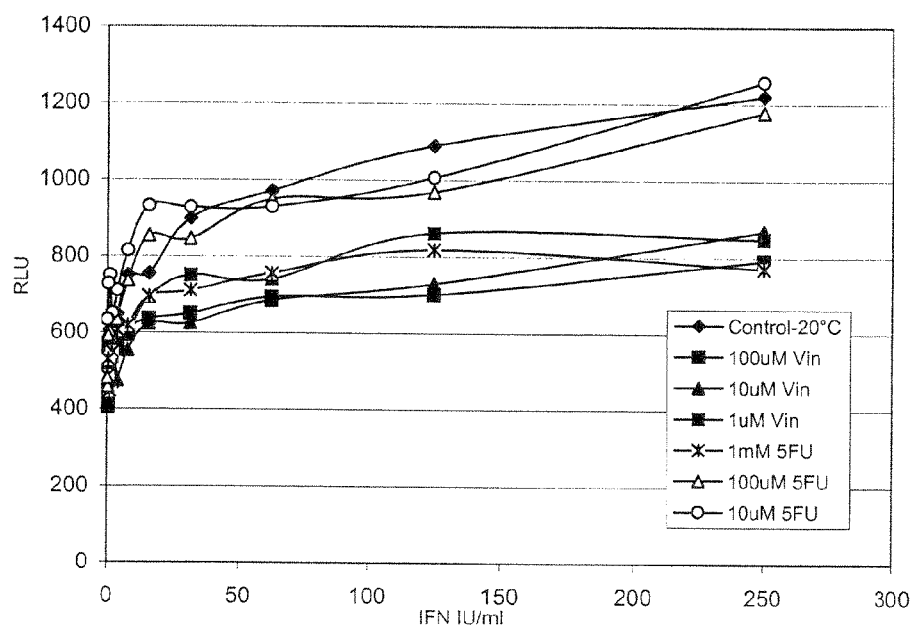
FIG. 12 is a graph showing the effect of vinblastine or 5-fluorouracil on interferon sensitivity of frozen cells. PIL5 cells were treated for 1 hour at 37° C. with 1.0, 10, or 100 μM vinblastine, or 10, 100 μM, or 1.0 mM 5-fluorouracil, centrifuged, and suspended in 50 μl of RPMI 1640 medium with 20% fetal bovine serum (FBS) and 10% dimethylsulfoxide (DMSO), and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 13:
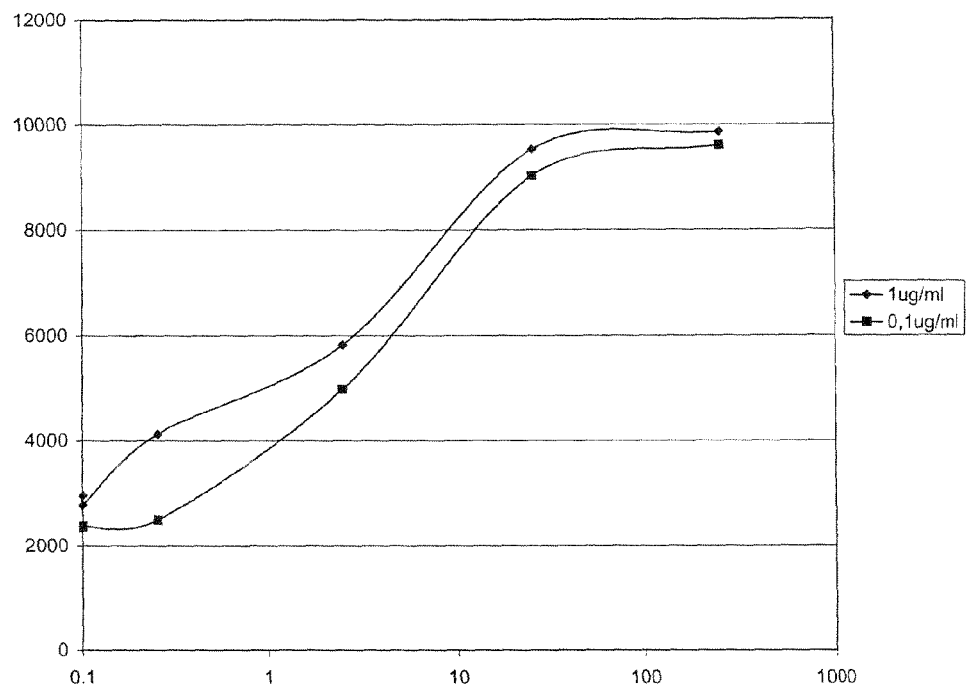
FIG. 13 is a graph showing the effect of vinblastine on interferon sensitivity of frozen cells. PIL5 cells were treated for 10 minutes at 37° C. with 0.1, or 1.0 μg/ml of vinblastine, centrifuged, and suspended in 25 μl of RPMI 1640 medium with 40% FBS and 10% glycerol, and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 14:
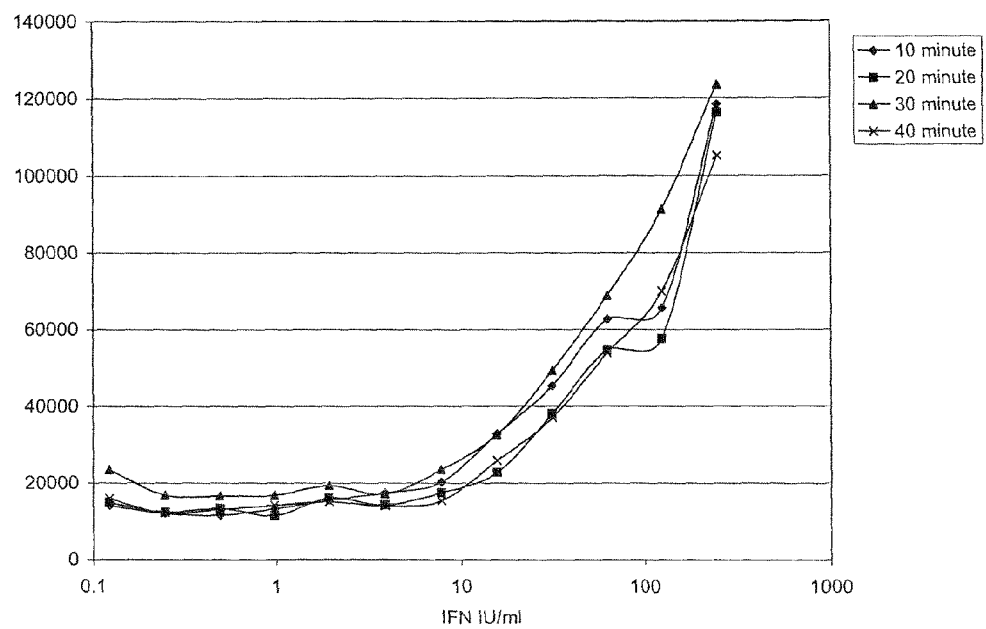
FIG. 14 is a graph showing the effect of time of treatment with vinblastine on interferon sensitivity of frozen cells. PIL5 cells were treated for 10, 20, 30, or 40 minutes at 37° C. with 1.0 μg/ml vinblastine, centrifuged, and suspended in 50 μl of RPMI 1640 medium with 20% FDS and 10% DMSO, and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 15:
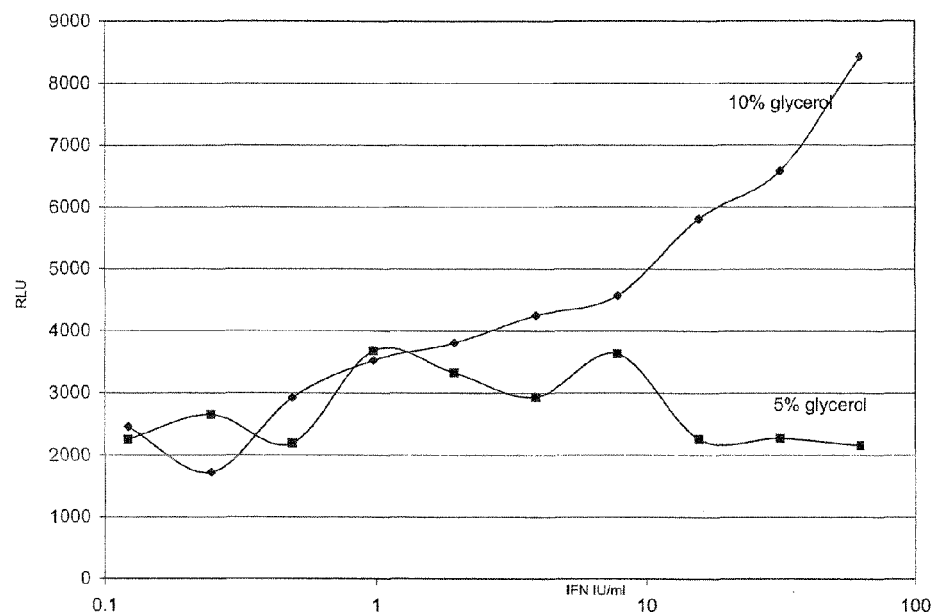
FIG. 15 is a graph showing the effect of glycerol concentration on interferon sensitivity of frozen cells. PIL5 cells were treated for 10 minutes at 37° C. with 100 μM vinblastine, centrifuged, and suspended in 25 μl of RPMI 1640 medium with 40% FBS and 5, or 10% glycerol, and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 16:
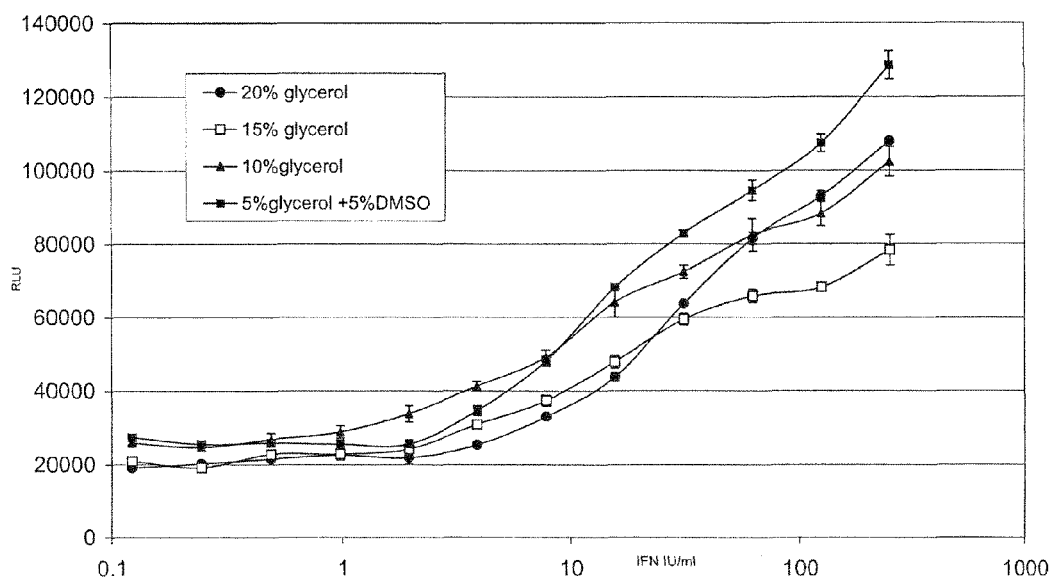
FIG. 16 is a graph showing the effect of glycerol concentration on the interferon sensitivity of frozen cells. PIL5 cells were treated for 10 minutes at 37° C. with 100 μM vinblastine, centrifuged, and suspended in 25 μl of RPMI 1640 medium with 40% FBS and 5, 10, 15, 20% glycerol, or 5% glycerol and 5% DMSO and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 17:
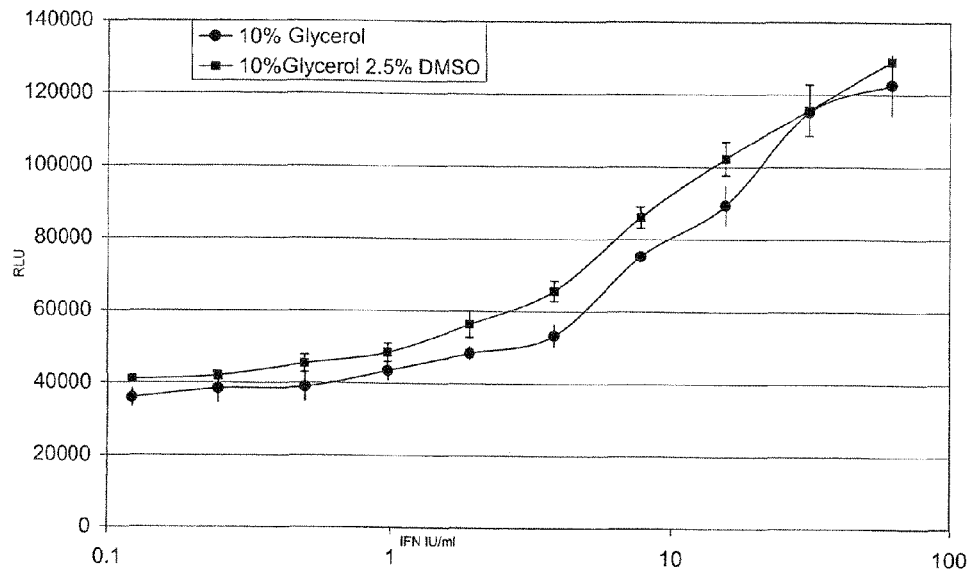
FIG. 17 is a graph showing the effect of glycerol in the presence or absence of DMSO on the interferon sensitivity of frozen cells. PIL5 cells were treated for 10 minutes at 37° C. with 100 μM vinblastine, centrifuged, and suspended in 25 μl of RPMI 1640 medium with 40% FBS and 10% glycerol, with or without 2.5% DMSO, and $2 \times 10^5$ cells were distributed into each well of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 18:
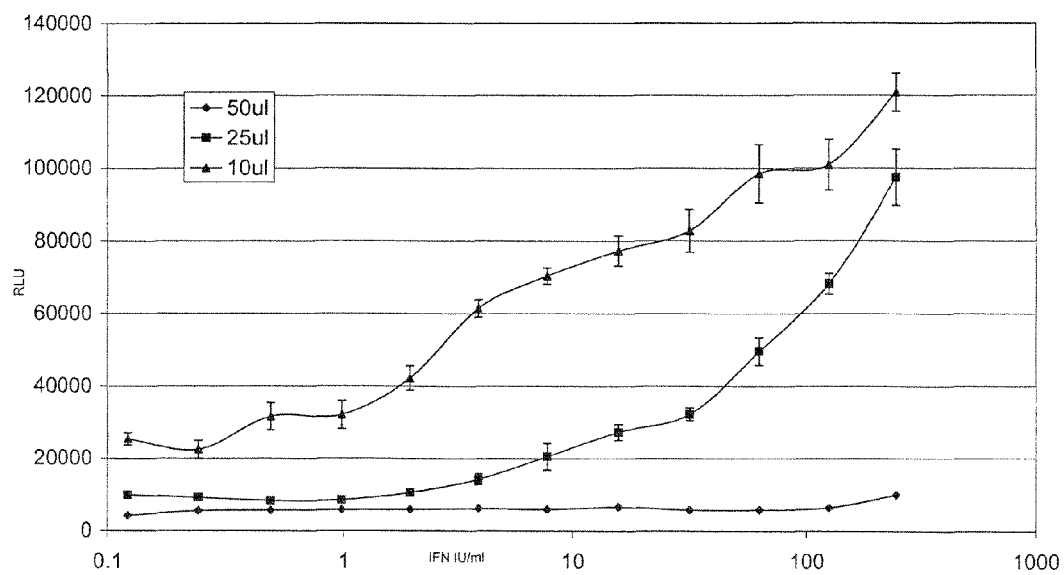
FIG. 18 is a graph showing the effect of cell density on the interferon sensitivity of frozen cells. PIL5 cells were treated for 10 minutes at 37° C. with 100 μM vinblastine, centrifuged, and $2 \times 10^5$ cells suspended in 10, 25, or 50 μl of RPMI 1640 medium with 40% FBS and 10% DMSO, and distributed into the wells of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 19:
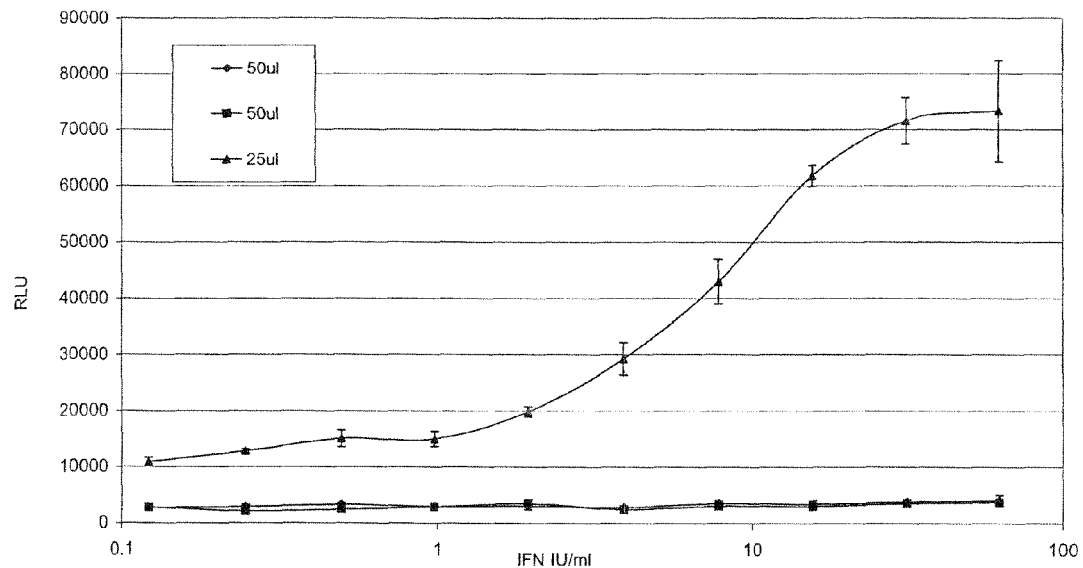
FIG. 19 is a graph showing the effect of cell density on the interferon sensitivity of frozen cells. PIL5 cells were treated for 10 minutes at 37° C. with 100 μM vinblastine, centrifuged, and $2 \times 10^5$ cells suspended in 25 or 50 μl of RPMI 1640 medium with 40% FBS and 10% DMSO, and distributed into the wells of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 20:
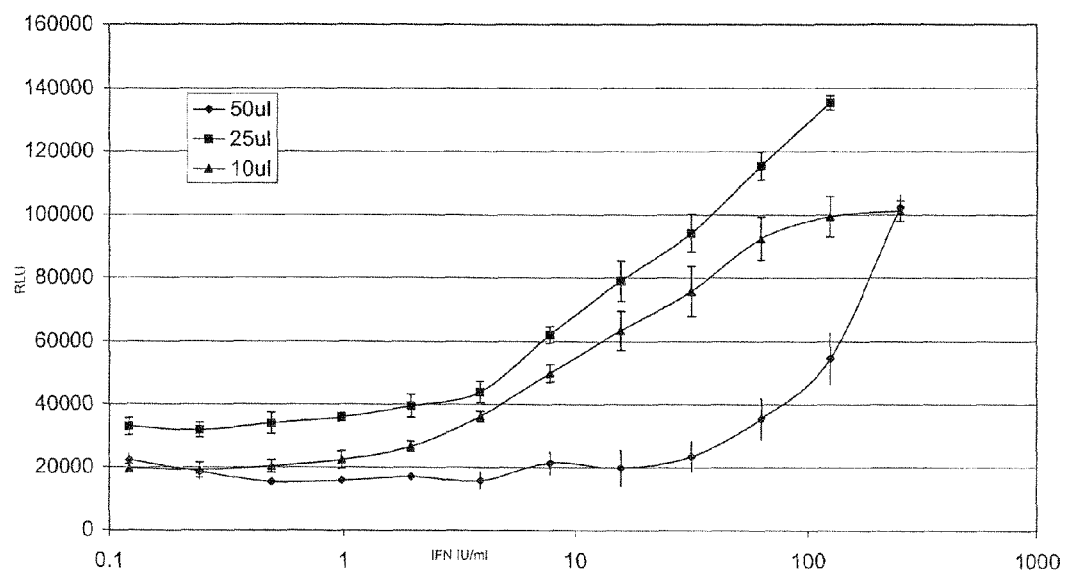
FIG. 20 is a graph showing the effect of cell density on the interferon sensitivity of frozen cells. PIL5 cells were treated for 10 minutes at 37° C. with 100 μM vinblastine, centrifuged, and $2 \times 10^5$ cells suspended in 10, 25, or 50 μl of RPMI 1640 medium with 40% FBS and 10% glycerol, and distributed into the wells of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.

Effect of Treatment with an Anti-Mitotic Agent and Subsequent Freezing on IFN Sensitivity PIL5 cells were suspended at a concentration of $2 \times 10^6$ cells/ml in RPMI 1640 medium plus 10% fetal bovine serum (FBS) and incubated at 37° C. for 1.0 hour in the presence of 100 μM vinblastine. The cells were then centrifuged at 800×g for 10 minutes, washed once with the same volume of RPMI 1640 medium with 10% FBS to remove vinblastine, and re-suspended in RPMI 1640 medium plus 40% fetal bovine serum, 10% glycerol and 2.5% dimethylsulfoxide (DMSO). The cell suspension ($10^5$ cells in a volume of 25 μl) is then distributed into the wells of a micro-titer plate (CulturePlate-96, Packard Biosciences, Inc., now part of PerkinElmer Life Sciences, Boston, Mass.) and stored at −20° C. until use. The micro-titer plates containing the frozen cells are then removed from the −20° C. freezer, thawed rapidly, preferably using a waterbath preset at 37° C., and 75 μl of the sample to be tested, or the IFN standard without serum, or negative control sample without serum, is added to a well of the micro-titer plate and incubated overnight at 37° C. One hundred micro-liters of LUCLIT PLUS (Packard Biosciences, Inc., Catalog #6016961, U.S. Pat. Nos. 5,283,179; 5,641,641; 5,650,289; and 5,814,471) or a similar reagent, which contains luciferin (D-(−)-2-(6'-hydroxy-2'-benzothiazolyl)-$\Delta^2$-thiazoline-4-carboxylic acid), ATP, buffer, $Mg^{+2}$, and preferably coenzyme A for enhancing the activity of luciferase and a thiol reagent/sulfhydryl compound for stabilizing luciferase, is added to each well of the micro-titer plate and the samples are read on a plate reading luminometer (LUMI-COUNT, Packard BioSciences, Inc.). PIL5 cells were found to retain full IFN sensitivity at one month after treatment with 100 μM vinblastine and freezing at −20° C. (FIG. 11). The results of this study have established a method for the development of the PIL5 IFN gene reporter assay in a commercially viable kit format with a current shelf-life of at least one month at −20° C. without loss of IFN sensitivity.

Studies on the effects of a variety of parameters, i.e., concentration of vinblastine, time of treatment with vinblastine, fetal bovine serum (FBS) concentration, glycerol concentration in the presence or absence of DMSO, SMSO concentration, cell density, on interferon sensitivity of frozen cells were conducted to determine optimal conditions. See FIGS. 12-20. It may not be apparent from the results shown in FIG. 12 why vinblastine instead of 5-FU was chosen as the more preferred anti-mitotic and pro-apoptotic agent for treatment of PIL5 cells prior to freezing. The reason is that although 5-FU was superior to vinblastine in terms of maintaining interferon sensitivity, 5-FU was not found to be sufficiently effective in preventing cell replication at the doses tested.

Figure 21:
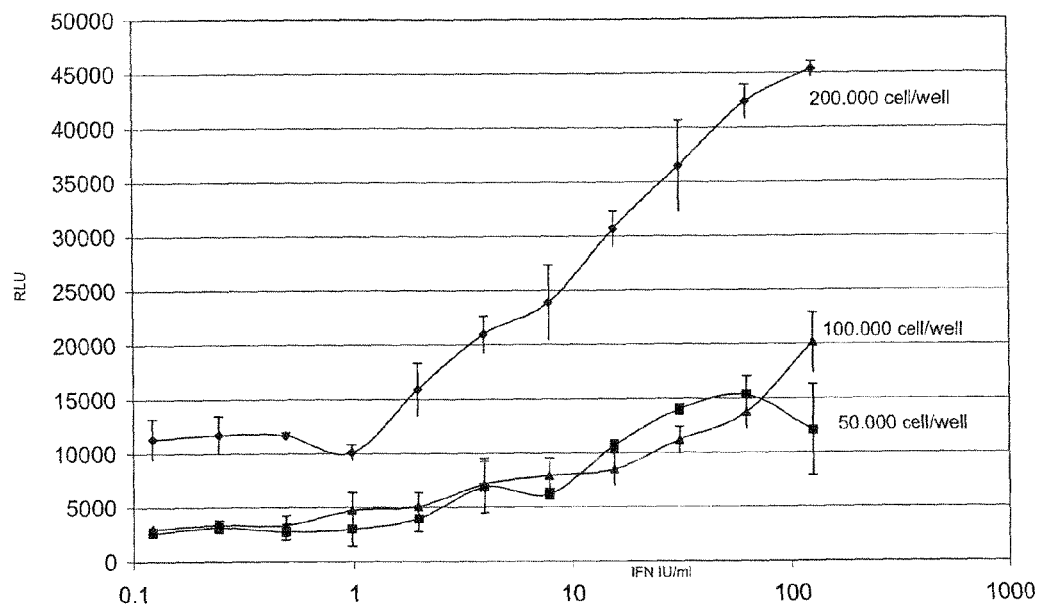
FIG. 21 is a graph showing the effect of cell number on interferon sensitivity following freezing. PIL5 cells were treated for 10 minutes at 37° C. with 100 μM vinblastine, centrifuged, and 0.5, 1.0, or $2 \times 10^5$ cells suspended in 10 μl of RPMI 1640 medium with 40% FBS and 10% glycerol, and distributed into the wells of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 22:
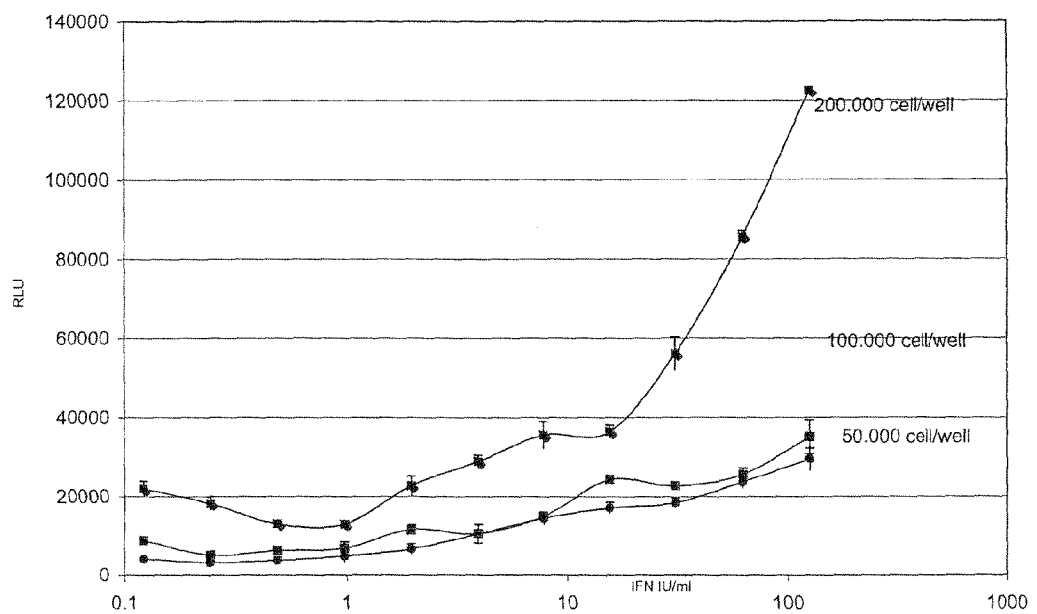
FIG. 22 is a graph showing the effect of cell number on interferon sensitivity following freezing. PIL5 cells were treated for 10 minutes at 37° C. with 100 μM vinblastine, centrifuged, and 0.5, 1.0, or $2 \times 10^5$ cells suspended in 10 μl of 40% FBS and distributed into the wells of a micro-titer culture plate and frozen at −80° C. After storage at −80° C. and subsequent storage at −20° C., the plate was thawed rapidly and a standard preparation of human IFN α was titrated in the luciferase gene reporter assay procedure described above.
Figure 23:
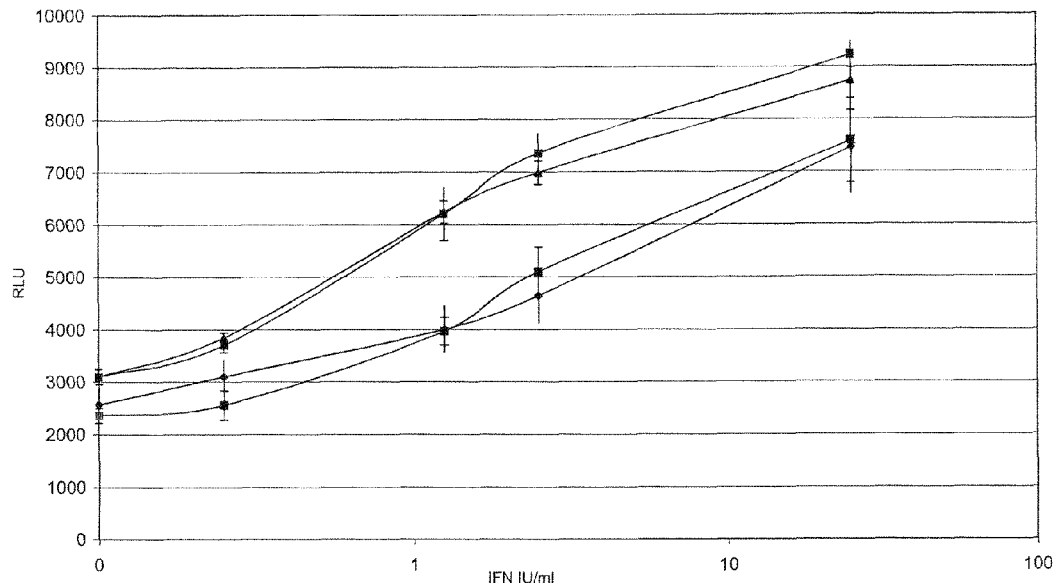
FIG. 23 is a graph showing the effect of freezing in a cryo-preservation ampoule or micro-titer plate on interferon sensitivity. PIL5 cells were treated for 10 minutes at 37° C.

FIGS. 21 and 22 show the effect of cell number on interferon sensitivity of the treated PIL5 cells following freezing, and FIG. 23 is a study on the effect of freezing in either a microtiter plate or in a cryopreservation ampoule/vial on interferon sensitivity of thawed treated PIL5 cells. A titration curve of a standard interferon preparation on treated PIL5 cells following freezing is presented in FIG. 24.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abramovich et al. (1994) Differential tyrosine phosphorylation of the IFNAR chain of the type I interferon receptor and of an associated surface protein in response to IFN-alpha and IFN-beta. *Embo J.* 13:5871.

Alton et al. (1979) Nucleotide sequence analysis of the chloramphenicol resistance transposon Tn9. *Nature* 282:864-869

Baldwin et al. (1984) Cloning of the luciferase structural genes from *Vibrio harveyi* and expression of bioluminescence in *Escherichia coli. Biochemistry* 23:3663-3667

Barbieri et al. (1994) Activation of the protein tyrosine kinase tyk2 by interferon alpha/beta. *Eur J. Biochem.* 223:427.

Basu et al. (1998) The antiviral action of interferon is potentiated by removal of the conserved IRTAM domain of the IFNAR1 chain of the interferon alpha/beta receptor: effects on JAK-STAT activation and receptor down-regulation. *Virology.* 242:14.

Bazan, (1990). Structural design and molecular evolution of a cytokine receptor superfamily. *Proc Natl Acad Sci USA.* 87:6934.

Bouche et al. (1987) Basic fibroblast growth factor enters the nucleolus and stimulates the transcription of ribosomal genes in ABAE cells undergoing G0 - - - G1 transition. *Proc. Natl. Acad. Sci. U.S.A.* 84:6770-6774

Boulter et al. (1986) Isolation of a cDNA clone coding for a possible neural nicotinic acetylcholine receptor alpha-subunit. *Nature* 319:368-374

Boulter et al. (1990) Alpha 3, alpha 5, and beta 4: three members of the rat neuronal nicotinic acetylcholine receptor-related gene family form a gene cluster. *J. Biol. Chem.* 265:4472-4482

Branca et al. (1981) Evidence that types I and II interferons have different receptors. *Nature.* 294:768.

Bunzow et al. (1988) Cloning and expression of a rat D2 dopamine receptor cDNA. *Nature* 336:783-787

Canosi et al. (1996) A highly precise reporter gene bioassay for type I interferon. *Journal of Immunological Methods* 199:69-76

Changelian et al. (1989) Structure of the NGFI-A gene and detection of upstream sequences responsible for its transcriptional induction by nerve growth factor. *Proc. Natl. Acad. Sci. USA* 86:377-381

Changelian et al. (1989) Structure of the NGFI-A gene and detection of upstream sequences responsible for its transcriptional induction by nerve growth factor. *Proc. Natl. Acad. Sci.* 86:377-381

Cleary et al. (1994) Knockout and reconstitution of a functional human type I interferon receptor complex. *Journal of Biological Chemistry.* 269:18747.

Cohen et al. (1995) Ligand-induced association of the type I interferon receptor components. *Mol Cell Biol.* 15:4208.

Colamonici et al. (1994) Direct binding to and tyrosine phosphorylation of the alpha subunit of the type I interferon receptor by p135tyk2 tyrosine kinase. *Mol. Cell. Biol.* 14:8133.

Comb et al. (1986) *Nature* 323:353-356

Constantinescu et al. (1994) Role of interferon alpha/beta receptor chain 1 in the structure and transmembrane signaling of the interferon alpha/beta receptor complex. *Proc Natl Acad Sci USA.* 91:9602.

Constantinescu et al. (1995) Expression and signaling specificity of the IFNAR chain of the type I interferon receptor complex. *Proc Natl Acad Sci USA.* 92:10487.

Cook et al. (1996) Differential responsiveness of a splice variant of the human type I interferon receptor to interferons. *J Biol Chem.* 271:13448.

Cutrone et al. (1997) Contributions of cloned type I interferon receptor subunits to differential ligand binding. *FEBS Lett.* 404:197.

Darnell et al. (1994) Jak-STAT pathways and transcriptional activation in response to IFNs and other extracellular signaling proteins. *Science.* 264:1415.

De Maeyer et al. (1988) Interferons and other regulatory cytokines. *John Wiley*, New york:69.

Deneris et al. (1988) Primary structure and expression of beta 2: a novel subunit of neuronal nicotinic acetylcholine receptors. *Neuron* 1:45-54

Deneris et al. (1989) Beta 3: a new member of nicotinic acetylcholine receptor gene family is expressed in brain. *J. Biol. Chem.* 264: 6268-6272 deWet et al. (1987) Firefly luciferase gene: structure and expression in mammalian cells. *Mol. Cell. Biol.* 7:725-737

Diaz et al. (1993) Nomenclature of the human interferon genes. *J Interferon Res.* 13:443.

Dixon et al. (1986) Cloning of the gene and cDNA for mammalian beta-adrenergic receptor and homology with rhodopsin. *Nature*

Domanski et al. (1995) Cloning and expression of a long form of the beta subunit of the interferon alpha beta receptor that is required for signaling. *J Biol Chem.* 270:21606.

Domanski et al. (1996) The type-I interferon receptor. The long and short of it. *Cytokine Growth Factor Rev.* 7:143.

Duvoisin et al. (1989) The functional diversity of the neuronal nicotinic acetylcholine receptors is increased by a novel subunit: beta 4. *Neuron* 3:487-496

Ellis et al. (1988) Sequence and expression of mRNAs encoding the alpha 1 and alpha 2 subunits of a DHP-sensitive calcium channel. *Science* 241:1661-1664

Engebrecht et al. (1984) Identification of genes and gene products necessary for bacterial bioluminescence. *PNAS* 1:4154-4158

Fiette et al. (1995) Theiler's virus infection of 129Sv mice that lack the interferon alpha/beta or interferon gamma receptors. *Journal of Experimental Medicine.* 181:2069.

Fink et al. (1988), The CGTCA sequence motif is essential for biological activity of the vasoactive intestinal peptide gene cAMP-regulated enhancer. *Proc. Natl. Acad. Sci.* 85:6662-6666

Frielle et al. (1987) Cloning of the cDNA for the human beta 1-adrenergic receptor. *Proc. Natl. Acad. Sci.* 84:7920-7924

Fu, (1992) A transcription factor with SH2 and SH3 domains is directly activated by an interferon alpha-induced cytoplasmic protein tyrosine kinase(s). *Cell.* 70:323.

Goldman et al. (1987) Members of a nicotinic acetylcholine receptor gene family are expressed in different regions of the mammalian central nervous system. *Cell* 48:965-973

Hall et al. (1983) *J. Mol. Appl. Gen.* 2:101

Hammerling et al. (1998) The S-gal interferon assay: a new, precise, and sensitive method. *Journal of Interferon and Cytokine Research* 18:451-460

Hollmann et al. (1989) Cloning by functional expression of a member of the glutamate receptor family. *Nature* 342:643-648

Horvath et al. (1995) A STAT protein domain that determines DNA sequence recognition suggests a novel DNA-binding domain Genes Dev. 9:984-994

Hwang et al. (1995) A null mutation in the gene encoding a type I interferon receptor component eliminates antiproliferative and antiviral responses to interferons alpha and beta and alters macrophage responses. *Proc Natl Acad Sci USA.* 92:11284.

Ihle, (1995) Cytokine receptor signalling. *Nature.* 377:591.

Jay et al. (1990) Primary structure of the gamma subunit of the DHP-sensitive calcium channel from skeletal muscle. *Science* 248:490-492

Johnson et al. (1986) *Cell* 47:545-554

Julius et al. (1988) Molecular characterization of a functional cDNA encoding the serotonin 1c receptor. *Science* 241: 558-564

Julius et al. (1990) The 5HT2 receptor defines a family of structurally distinct but functionally conserved serotonin receptors. *PNAS* 87:928-932

Kayano et al, (1988) Primary structure of rat brain sodium channel III deduced from the cDNA sequence. *FEBS Lett.* 228:187-194

Kobilka et al. (1987) An intronless gene encoding a potential member of the family of receptors coupled to guanine nucleotide regulatory proteins. *Nature* 329:75-79

Kobilka et al. (1987) Cloning, sequencing, and expression of the gene coding for the human platelet alpha 2-adrenergic receptor. *Science* 238:650-656

Lallemand et al. (1996) Constitutive expression of specific interferon isotypes in peripheral blood leukocytes from normal individuals and in promonocytic U937 cells. *J Leukoc Biol.* 60:137-46

Langer et al. (1996) Interferon receptors. *Biotherapy.* 8:163

Levitan et al. (1988) Structural and functional basis for GABAA receptor heterogeneity. *Nature* 335:76-79

Levy et al. (1988) Interferon-induced nuclear factors that bind a shared promoter element correlate with positive and negative control Genes Dev. 2:383-393

Lewis, (1995) A sensitive biological assay for interferons. *Journal of Immunological Methods* 185:9-17

Lim et al. (1993) Cloning and characterization of a bovine alpha interferon receptor. *Biochim Biophys Acta.* 1173: 314.

Lleonart et al., (1990) A novel, quantitative bioassay for type I interferon using a recombinant indicator cell line. *Biotechnology* 8:1263-1267

Lutfalla et al. (1992) The structure of the human interferon alpha/beta receptor gene. *J Biol. Chem.* 267:2802.

Lutfalla et al. (1995) Mutant U5A cells are complemented by an interferon-alpha beta receptor subunit generated by alternative processing of a new member of a cytokine receptor gene cluster. *Embo J.* 14:5100.

McKinnon, D. (1989) Isolation of a cDNA clone coding for a putative second potassium channel indicates the existence of a gene family. *J. Biol. Chem.* 264:8230-8236

Merlin et al. (1985) 125I-labelled human interferons alpha, beta and gamma: comparative receptor-binding data. *J Gen Virol.* 66:1149.

Montminy et al. (1986), Identification of a cyclic-AMP-responsive element within the rat somatostatin gene. *Proc. Natl. Acad. Sci.* 83:6682-6686

Mouchel-Vielh et al. (1992). Specific antiviral activities of the human alpha interferons are determined at the level of receptor (IFNAR) structure. *FEBS Lett.* 313:255.

Muller et al. (1994) Functional role of type I and type II interferons in antiviral defense. *Science.* 264:1918.

Noda et al. (1986) *Nature* 320:188-192

Novick et al. (1994) The human interferon alpha/beta receptor: characterization and molecular cloning. *Cell.* 77:391.

Perry et al., (1999) Cloning of interferon-stimulated gene 17: The promoter and nuclear proteins that regulate transcription. *Molecular Endocrinology,* 13:1197-1206

Pestka et al. (1987) Interferons and their actions. *A. Rev. Biochem.* 56:727.

Platanias et al. (1994) Tyrosine phosphorylation of the alpha and beta subunits of the type I interferon receptor. Interferon-beta selectively induces tyrosine phosphorylation of an alpha subunit-associated protein. *J. Biol. Chem.* 269: 17761.

Pritchett et al. (1989) Importance of a novel GABAA receptor subunit for benzodiazepine pharmacology. *Nature* 338:582-585

Rider et al. (2003) A B cell-based sensor for rapid identification of pathogens. *Science* 301:213-215

Russell-Harde et al. (1995) Reconstitution of a high affinity binding site for type I interferons. *J Biol Chem.* 270:26033.

Ruth et al. (1989) Primary structure of the beta subunit of the DHP-sensitive calcium channel from skeletal muscle. *Science* 245:1115-1118

Schindler et al. (1992) Interferon-dependent tyrosine phosphorylation of a latent cytoplasmic transcription factor [see comments]. *Science.* 257:809.

Schofield et al. (1987) Sequence and functional expression of the GABAA receptor shows a ligand-gated receptor superfamily. *Nature* 328:221-227

Schumacher et al. (1994) The chicken Mx promoter contains an ISRE motif and confers interferon inducibility to a reporter gene in chick and monkey cells. *Virology* 15:203 (1):144-8

Sheng et al. (1990) The regulation and function of c-fos and other immediate early genes in the nervous system. *Neuron* 4:477-485

Shivers, B. D. (1989) *Neuron* 3:327-337

Short et al. (1986) *J. Biol. Chem.* 261:9721-9726

Steinhoff et al. (1995) Antiviral protection by vesicular stomatitis virus-specific antibodies in alpha/beta interferon receptor-deficient mice. *Journal of Virology.* 69:2153.

Stormann et al. (1990) Molecular cloning and expression of a dopamine D2 receptor from human retina. *Molec. Pharm.* 37:1-6

Tanabe et al. (1987) Primary structure of the receptor for calcium channel blockers from skeletal muscle. *Nature* 328:313-E318

Taniguchi, (1995) Cytokine signaling through nonreceptor protein tyrosine kinases. *Science.* 268:251.

Tempel et al. (1988) Cloning of a probable potassium channel gene from mouse brain. *Nature* 332:837-839

Thoreau et al. (1991) Structural symmetry of the extracellular domain of the cytokine/growth hormone/prolactin receptor family and interferon receptors revealed by hydrophobic cluster analysis. *FEBS Lett.* 282:26.

Toh et al. (1989) Isolation and characterization of a rat liver alkaline phosphatase gene. A single gene with two promoters. *Eur. J. Biochem.* 182:231-238

Uddin et al. (1995) Interaction of the transcriptional activator Stat-2 with the type I interferon receptor. *J Biol Chem.* 270:24627.

Uze et al. (1990) Genetic transfer of a functional human interferon alpha receptor into mouse cells: cloning and expression of its cDNA. *Cell.* 60:225.

Uze et al. (1992) Behavior of a cloned murine interferon alpha/beta receptor expressed in homospecific or heterospecific background. *Proc Natl Acad Sci USA.* 89:4774.

Uzé et al. (1995) Alpha and beta interferons and their receptor and their friends and relations. *Journal of Interferon & Cytokine Research.* 15:3.

van den Broek et al. (1995) Antiviral defense in mice lacking both alpha/beta and gamma interferon receptors. *Journal of Virology.* 69:4792.

Vandenbroek et al. (1995) Immune defence in mice lacking type I and/or type II interferon receptors. *Immunol Rev.* 148:5.

Velazquez et al. (1995) Distinct domains of the protein tyrosine kinase tyk2 required for binding of interferon-alpha/beta and for signal transduction. *J Biol Chem.* 270: 3327.

Wada et al. (1988) Functional expression of a new pharmacological subtype of brain nicotinic acetylcholine receptor. *Science* 240:330-334

Yan et al. (1996) Molecular characterization of an alpha interferon receptor 1 subunit (IFNaR1) domain required for TYK2 binding and signal transduction. *Mol Cell Biol.* 16:2074.

Yan et al. (1996) Phosphorylated interferon-alpha receptor 1 subunit (IFNaR1) acts as a docking site for the latent form of the 113 kDa STAT2 protein. *EMBO J.* 15:1064.

Yeh et al. (1987) Ultrastructural localization of a platelet-derived growth factor/v-sis-related protein(s) in cytoplasm and nucleus of simian sarcoma virus-transformed cells. *Proc. Natl. Acad. Sci. U.S.A.* 84:2317-2321

Ymer et al. (1989) GABAA receptor beta subunit heterogeneity: functional expression of cloned cDNAs. *EMBO J.* 8:1665-1670

Zlokarnik et al. (1998) Quantitation of transcription and clonal selection of single living cells with S-lactamase as reporter. *Science* 279:84-88.

---

What is claimed is:

1. In a mammalian cell line transformed with a reporter gene construct comprising a nucleotide sequence encoding a reporter gene product operatively linked to a transcriptional control element that is activated as part of a signal transduction pathway activated by the interaction of an extracellular signal with a cell surface molecule or complex, the improvement wherein said cell line maintains the activity of said signal transduction pathway for at least about 1 hour after having been frozen and thawed but will lose said activity, under the same conditions under which the activity was maintained for at least about 1 hour, in no more than about 30 days after having been frozen and thawed.

2. The mammalian cell line of claim 1 in a frozen state, wherein said cell line maintains the activity of said signal transduction pathway for at least about 1 hour after being thawed but will lose said activity, under the same conditions under which the activity was maintained for at least about 1 hour, in no more than about 30 days after being thawed.

3. The mammalian cell line of claim 1, wherein the period of time after having been frozen and thawed before which the cell line will lose said activity is no more than about 24 hours.

4. The mammalian cell line of claim 1, wherein the period of time after having been frozen and thawed before which the cell line will lose said activity is no more than 14 days under said conditions, after having been frozen and thawed.

5. The mammalian cell line of claim 1, wherein the conditions under which the activity was maintained for at least about 1 hour are those in which the temperature is at room temperature.

6. The mammalian cell line of claim 1, wherein said cell surface molecule is a cell surface receptor.

7. The mammalian cell line of claim 6, wherein said cell surface receptor is selected from the group consisting of a cytokine receptor, a growth factor receptor, a hormone receptor, a neuro receptor, a T cell receptor, an antigen receptor, and a complement receptor.

8. The mammalian cell line of claim 1 which is a human cell line.

9. The mammalian cell line of claim 8 which is a human promonocytic cell line.

10. A kit for determining the level in a sample of a molecule that activates the signal transduction activity of a cell surface protein, comprising:
   a testing device having a plurality of wells; and
   the mammalian cell line of claim 1.

11. The kit of claim 10, wherein said testing device is a microtiter plate.

12. The kit of claim 10, wherein the mammalian cell line is disposed in the wells of said testing device.

13. A kit for determining the level in a sample of a molecule that activates the signal transduction activity of a cell surface protein, comprising:
   a testing device having a plurality of wells; and
   the frozen mammalian cell line of claim 2.

14. A composition comprising the mammalian cell line of claim 1 and a cryopreservative.

15. A method for preparing the mammalian cell line of claim 1, comprising:
   transforming a mammalian cell line with a reporter gene construct comprising a nucleotide sequence encoding a reporter gene product operatively linked to a transcriptional control element that is activated as part of a signal transduction pathway activated by the interaction of an extracellular signal with a cell surface molecule or complex; and
   treating said transformed cell line with an anti-mitotic and pro-apoptotic agent such that it will maintain said signal transduction activity for at least about 1 hour but will lose said signal transduction activity, under the same conditions under which the activity was maintained for at least about 1 hour, in no more than about 30 days under said conditions to obtain the cell line of claim 1.

16. The method of claim 15, wherein said anti-mitotic and pro-apoptotic agent is selected from the group consisting of vinblastine, 5-fluorouracil, and γ-irradiation.

17. The method of claim 15, further comprising the step of freezing the treated cell line at a temperature and under conditions such that it will resume signal transduction after thawing.

18. The method of claim 17, wherein said step of freezing is carried out at a temperature in a range of about −20° C. to about −200° C. and the cells are subsequently stored at a temperature of about −20° C.

19. The method of claim 17, wherein said step of freezing is carried out at a temperature of about −80° C.

20. The method of claim 19, further comprising resuspending the treated cell line in a solution containing a cryopreservative before said step of freezing.

21. A method for determining the presence and/or the level in a sample of a molecule that activates the signal transduction activity of a cell surface protein, comprising:
   incubating the mammalian cell line of claim 1, within the period of time that said cell line maintains the activity of said signal transduction pathway, with a sample in which the presence and/or the level of the molecule that activates the signal transduction activity of a cell surface protein and serves as the extracellular signal is sought to be determined; and
   determining the level of expression of the reporter gene product to thereby determine the presence and/or the level in the sample of the molecule that activates the signal transduction activity of the cell surface protein.

22. The method of claim 21, wherein the cell surface protein is a cell surface receptor.

23. A method for determining the presence and/or the level in a sample of a molecule that activates the signal transduction activity of a cell surface protein, comprising:
   thawing the frozen cell line of claim 2;
   within the period of time that said thawed cell line maintains said signal transduction activity, incubating the thawed cell line with a sample in which the presence and/or the level of a molecule that activates the signal transduction activity of the cell surface protein and serves as the extracellular signal is sought to be determined; and
   determining the level of expression of the reporter gene product to thereby determine the presence and/or the level in the sample of the molecule that activates the signal transduction activity of the cell surface protein.

24. The method of claim 23, wherein the cell surface protein is a cell surface receptor.

* * * * *